(12) United States Patent
Woodell-May et al.

(10) Patent No.: US 9,758,806 B2
(45) Date of Patent: Sep. 12, 2017

(54) ACELLULAR COMPOSITIONS FOR TREATING INFLAMMATORY DISORDERS

(71) Applicant: Biomet Biologics, LLC, Warsaw, IN (US)

(72) Inventors: Jennifer E. Woodell-May, Warsaw, IN (US); Joel C. Higgins, Claypool, IN (US); Michael D. Leach, Warsaw, IN (US); Krista O'Shaughnessey, Pierceton, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 304 days.

(21) Appl. No.: 13/837,005

(22) Filed: Mar. 15, 2013

(65) Prior Publication Data

US 2014/0274893 A1 Sep. 18, 2014

(51) Int. Cl.
*A61K 38/00* (2006.01)
*A61K 38/17* (2006.01)
*A61K 38/18* (2006.01)
*A61K 38/19* (2006.01)
*A61K 38/20* (2006.01)
*A61K 45/06* (2006.01)
*C12P 21/02* (2006.01)

(52) U.S. Cl.
CPC .............. *C12P 21/02* (2013.01); *A61K 38/00* (2013.01); *A61K 38/177* (2013.01); *A61K 38/1793* (2013.01); *A61K 38/18* (2013.01); *A61K 38/1808* (2013.01); *A61K 38/1833* (2013.01); *A61K 38/1858* (2013.01); *A61K 38/19* (2013.01); *A61K 38/191* (2013.01); *A61K 38/2006* (2013.01); *A61K 45/06* (2013.01)

(58) Field of Classification Search
CPC ............ A61K 38/1793; A61K 38/1858; A61K 38/1808; A61K 38/2006; A61K 38/191; A61K 38/18; A61K 38/1833; A61K 378/177; A61K 38/19; A61K 45/06
See application file for complete search history.

(56) References Cited

U.S. PATENT DOCUMENTS

| | | | |
|---|---|---|---|
| 4,708,799 A | 11/1987 | Gerlach et al. |
| 4,853,137 A | 8/1989 | Ersson |
| 5,075,222 A | 12/1991 | Hannum et al. |
| 5,359,032 A | 10/1994 | Dayer et al. |
| 5,571,418 A | 11/1996 | Lee et al. |
| 5,585,007 A | 12/1996 | Antanavich et al. |
| 5,599,558 A | 2/1997 | Gordinier et al. |
| 5,707,331 A | 1/1998 | Wells et al. |
| 5,788,662 A | 8/1998 | Antanavich et al. |
| 5,792,450 A | 8/1998 | Wilson et al. |
| 5,842,477 A | 12/1998 | Naughton et al. |
| 5,846,427 A | 12/1998 | Kessler et al. |
| 6,063,297 A | 5/2000 | Antanavich et al. |
| 6,096,728 A | 8/2000 | Collins et al. |
| 6,214,338 B1 | 4/2001 | Antanavich et al. |
| 6,287,558 B1 | 9/2001 | Lanza et al. |
| 6,337,072 B1 | 1/2002 | Ford et al. |
| 6,398,972 B1 | 6/2002 | Blasetti et al. |
| 6,599,873 B1 | 7/2003 | Sommer et al. |
| 6,623,472 B1 | 9/2003 | Reincke et al. |
| 6,649,072 B2 | 11/2003 | Brandt et al. |
| 6,713,246 B1 | 3/2004 | Reinecke et al. |
| 6,759,188 B2 | 7/2004 | Reinecke et al. |
| 6,790,371 B2 | 9/2004 | Dolecek |
| 6,811,777 B2 | 11/2004 | Mishra |
| 6,835,377 B2 | 12/2004 | Goldberg et al. |
| 6,905,612 B2 | 6/2005 | Dorian et al. |
| 7,011,852 B2 | 3/2006 | Sukavaneshvar et al. |
| 7,166,283 B2 | 1/2007 | Tsuji et al. |
| 7,179,391 B2 | 2/2007 | Leach et al. |
| 7,223,346 B2 | 5/2007 | Dorian et al. |
| 7,374,678 B2 | 5/2008 | Leach et al. |
| 7,465,293 B2 | 12/2008 | Reinecke et al. |
| 7,470,371 B2 | 12/2008 | Dorian et al. |
| 7,553,413 B2 | 6/2009 | Dorian et al. |
| 7,608,258 B2 | 10/2009 | Mishra |
| 7,678,385 B2 | 3/2010 | Reddi |
| 7,694,828 B2 | 4/2010 | Swift et al. |
| 7,708,152 B2 | 5/2010 | Dorian et al. |
| 7,806,276 B2 | 10/2010 | Leach et al. |

(Continued)

FOREIGN PATENT DOCUMENTS

| | | |
|---|---|---|
| AU | 748575 B2 | 6/2002 |
| CA | 2772084 C | 10/2016 |

(Continued)

OTHER PUBLICATIONS

Dinarello, C.A. Interleukin-1 in the pathogenesis and treatment of inflammatory diseases. Blood, 2011, vol. 117(14), p. 3720-3732.*

Woodell-May, J. et al. Autologous protein solution inhibits MMP-13 production by IL-1b and TNFa-stimulated human articular chrondrocytes. J. Orthopaedic Research, 2011, vol. 29, p. 1320-1326.*

Dinarello, C.A. Interleukin-1 in the pathogenesis and treatment of inflammatory diseases. Blood, 2011, vol. 117, No. 14, p. 3720-3732.*

Feige, U. et al. Anti-interleukin-1 and anti-tumor necrosis factor-a synergistically inhibit adjuvant arthritis in Lewis rats. CMLS Cellular and Molecular Life Sciences, 2000, vol. 57, p. 1457-1470.*

Kim S.J. et al. Development of a novel sustained release formulation of recombinant human growth homrone using sodium hyaluronate microparticles. J. Controlled Release, 2005, vol. 104, p. 323-335.*

(Continued)

*Primary Examiner* — Robert Landsman
*Assistant Examiner* — Bruce D Hissong
(74) *Attorney, Agent, or Firm* — Schwegman Lundberg & Woessner, P.A.

(57) ABSTRACT

Acellular compositions for treating inflammation, comprising two or more of IL1-ra, sTNF-R1, sTNF-RII, IGF-I, EGF, HGF, PDGF-AB, PDGF-BB, VEGF, TGF-β1, and sIL-1RII. Components of the acellular compositions may be derived from biologic materials, such as blood clots and urine. Components may also be obtained from cell cultures.

28 Claims, 2 Drawing Sheets

(56) References Cited

U.S. PATENT DOCUMENTS

| | | |
|---|---|---|
| 7,845,499 B2 | 12/2010 | Higgins et al. |
| 7,867,765 B2 | 1/2011 | Faustman et al. |
| 7,901,344 B2 | 3/2011 | Yoo |
| 7,901,584 B2 | 3/2011 | Dorian et al. |
| 7,914,689 B2 | 3/2011 | Higgins et al. |
| 7,992,725 B2 | 8/2011 | Leach et al. |
| 8,048,297 B2 | 11/2011 | Leach et al. |
| 8,048,321 B2 | 11/2011 | Leach et al. |
| 8,093,211 B2 | 1/2012 | Tennenbaum et al. |
| 8,202,539 B2 | 6/2012 | Behnam et al. |
| 8,753,690 B2 | 6/2014 | Higgins et al. |
| 8,992,862 B2 | 3/2015 | Leach et al. |
| 9,011,800 B2 | 4/2015 | Leach et al. |
| 9,119,829 B2 | 9/2015 | Higgins et al. |
| 9,308,224 B2 | 4/2016 | Higgins et al. |
| 2001/0016195 A1 | 8/2001 | Tobinick |
| 2001/0053764 A1 | 12/2001 | Sims et al. |
| 2002/0009454 A1 | 1/2002 | Boone et al. |
| 2002/0077276 A1 | 6/2002 | Fredeking et al. |
| 2002/0119179 A1 | 8/2002 | Rezania et al. |
| 2003/0055511 A1 | 3/2003 | Schryver et al. |
| 2003/0091536 A1 | 5/2003 | Frisbie et al. |
| 2003/0099650 A1 | 5/2003 | Ho et al. |
| 2003/0138910 A1 | 7/2003 | Reinecke et al. |
| 2003/0194397 A1 | 10/2003 | Mishra |
| 2003/0205538 A1 | 11/2003 | Dorian et al. |
| 2004/0120942 A1 | 6/2004 | McGinnis et al. |
| 2004/0182795 A1 | 9/2004 | Dorian et al. |
| 2004/0219182 A1 | 11/2004 | Gomes et al. |
| 2004/0251217 A1 | 12/2004 | Leach et al. |
| 2004/0258671 A1 | 12/2004 | Watkins |
| 2005/0059589 A1* | 3/2005 | Mullarkey ............... 514/12 |
| 2005/0084962 A1 | 4/2005 | Simon |
| 2005/0100536 A1 | 5/2005 | Mishra |
| 2005/0109716 A1 | 5/2005 | Leach et al. |
| 2005/0152905 A1 | 7/2005 | Omoigui |
| 2005/0186120 A1 | 8/2005 | Dorian et al. |
| 2005/0196874 A1 | 9/2005 | Dorian et al. |
| 2005/0197293 A1 | 9/2005 | Mellis et al. |
| 2006/0046960 A1 | 3/2006 | McKay et al. |
| 2006/0051865 A1 | 3/2006 | Higgins et al. |
| 2006/0057223 A1 | 3/2006 | DiMauro et al. |
| 2006/0057693 A1 | 3/2006 | Simon |
| 2006/0121002 A1 | 6/2006 | Rolland et al. |
| 2006/0171948 A1 | 8/2006 | Weinstein et al. |
| 2006/0175244 A1 | 8/2006 | Dorian et al. |
| 2006/0175268 A1 | 8/2006 | Dorian et al. |
| 2006/0263408 A1 | 11/2006 | Rezania et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0027082 A1 | 2/2007 | Hasty et al. |
| 2007/0075016 A1 | 4/2007 | Leach |
| 2007/0092494 A1 | 4/2007 | Higgins et al. |
| 2007/0207161 A1 | 9/2007 | Ralph |
| 2008/0011684 A1 | 1/2008 | Dorian et al. |
| 2008/0019964 A1 | 1/2008 | Olmarker et al. |
| 2008/0064626 A1 | 3/2008 | Zanella |
| 2008/0193424 A1 | 8/2008 | McKale et al. |
| 2008/0217263 A1 | 9/2008 | Higgins et al. |
| 2008/0268064 A1 | 10/2008 | Woodell-May |
| 2008/0269762 A1 | 10/2008 | Simon et al. |
| 2008/0283474 A1 | 11/2008 | Leach et al. |
| 2008/0300181 A1 | 12/2008 | Wang et al. |
| 2008/0306431 A1 | 12/2008 | Yoo |
| 2009/0014391 A1 | 1/2009 | Leach et al. |
| 2009/0047242 A1 | 2/2009 | Reinecke et al. |
| 2009/0101599 A1 | 4/2009 | Dorian et al. |
| 2009/0112146 A1 | 4/2009 | Wratten et al. |
| 2009/0181019 A1 | 7/2009 | Solinger |
| 2009/0191217 A1 | 7/2009 | de Wildt et al. |
| 2009/0192528 A1 | 7/2009 | Higgins et al. |
| 2009/0220482 A1* | 9/2009 | Higgins et al. ............ 424/94.64 |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2009/0263319 A1 | 10/2009 | Wohabrebbi et al. |
| 2009/0317439 A1 | 12/2009 | Turzi et al. |
| 2010/0008992 A1 | 1/2010 | Ichim |
| 2010/0015129 A1 | 1/2010 | Abramson et al. |
| 2010/0055087 A1 | 3/2010 | Higgins et al. |
| 2010/0125236 A1 | 5/2010 | Bare et al. |
| 2010/0140182 A1 | 6/2010 | Chapman et al. |
| 2010/0198130 A1 | 8/2010 | Swift et al. |
| 2010/0226909 A1 | 9/2010 | Hecker et al. |
| 2010/0256595 A1 | 10/2010 | Leach et al. |
| 2011/0052561 A1 | 3/2011 | Hoeppner |
| 2011/0059082 A1 | 3/2011 | Germer et al. |
| 2011/0059083 A1 | 3/2011 | Aigner et al. |
| 2011/0059084 A1 | 3/2011 | Osterroth et al. |
| 2011/0129441 A1 | 6/2011 | Lentz |
| 2011/0147929 A1 | 6/2011 | Roy et al. |
| 2011/0189172 A1 | 8/2011 | Solinger et al. |
| 2011/0192804 A1 | 8/2011 | Landrigan et al. |
| 2011/0268708 A1 | 11/2011 | Lin et al. |
| 2012/0027746 A1 | 2/2012 | Dorian et al. |
| 2012/0093936 A1 | 4/2012 | Lindenberg et al. |
| 2012/0150086 A1 | 6/2012 | Cohen |
| 2012/0172836 A1 | 7/2012 | Higgins et al. |
| 2013/0119549 A1 | 5/2013 | Cheng et al. |
| 2013/0178425 A1 | 7/2013 | Higgins et al. |
| 2013/0259951 A1 | 10/2013 | O'Connell, Jr. |
| 2014/0242045 A1 | 8/2014 | Higgins et al. |
| 2014/0271587 A1 | 9/2014 | Landrigan et al. |
| 2014/0271588 A1 | 9/2014 | Landrigan et al. |
| 2014/0271589 A1 | 9/2014 | Matuska et al. |
| 2014/0271870 A1 | 9/2014 | O'Shaughnessey et al. |
| 2014/0274894 A1 | 9/2014 | Leach et al. |
| 2014/0274895 A1 | 9/2014 | Binder et al. |
| 2014/0275497 A1 | 9/2014 | Leach et al. |
| 2014/0349388 A1 | 11/2014 | Dorian et al. |
| 2014/0356446 A1 | 12/2014 | Leach et al. |
| 2015/0141332 A1 | 5/2015 | Toler |
| 2015/0147300 A1 | 5/2015 | Woodell-May et al. |
| 2016/0000870 A1 | 1/2016 | Higgins et al. |
| 2016/0017010 A1 | 1/2016 | Higgins et al. |
| 2016/0074479 A1 | 3/2016 | Serbousek et al. |
| 2016/0136245 A1 | 5/2016 | Toler et al. |
| 2016/0166645 A1 | 6/2016 | Matuska et al. |

FOREIGN PATENT DOCUMENTS

| | | |
|---|---|---|
| CN | 1321103 A | 11/2001 |
| CN | 1322146 A | 11/2001 |
| CN | 105209478 A | 12/2015 |
| CN | 105338990 A | 2/2016 |
| CN | 105339007 A | 2/2016 |
| CN | 105358161 A | 2/2016 |
| CN | 105358162 A | 2/2016 |
| CN | 105492015 A | 4/2016 |
| EP | 0417818 A1 | 3/1991 |
| EP | 2186877 A2 | 5/2010 |
| EP | 2968409 A1 | 1/2016 |
| EP | 2968412 A1 | 1/2016 |
| EP | 2470163 B1 | 9/2016 |
| JP | 069684 A | 1/1994 |
| JP | 07101874 A | 4/1995 |
| JP | 2000189407 A | 7/2000 |
| JP | 2001500472 A | 1/2001 |
| JP | 2002509529 A | 3/2002 |
| JP | 2003525696 A | 9/2003 |
| JP | 2007105186 A | 4/2007 |
| JP | 2007509601 A | 4/2007 |
| JP | 2009155234 A | 7/2009 |
| JP | 5551250 B2 | 7/2014 |
| WO | WO-9108285 A1 | 6/1991 |
| WO | 9905989 A2 | 2/1999 |
| WO | 9967277 A1 | 12/1999 |
| WO | 03063799 A2 | 8/2003 |
| WO | 03080104 A2 | 10/2003 |
| WO | 03088905 A2 | 10/2003 |
| WO | 2004/009207 | 1/2004 |
| WO | WO-2004065564 A2 | 8/2004 |

(56) References Cited

FOREIGN PATENT DOCUMENTS

| WO | 2006/043972 A1 | 4/2006 |
|---|---|---|
| WO | 2007/121538 A1 | 11/2007 |
| WO | 2007/128973 A2 | 11/2007 |
| WO | 2008/021237 A1 | 2/2008 |
| WO | WO-2009108890 A1 | 9/2009 |
| WO | WO-2010149164 A2 | 12/2010 |
| WO | 2011/031553 A2 | 3/2011 |
| WO | WO-2011031524 A3 | 3/2011 |
| WO | WO-2011031525 A1 | 3/2011 |
| WO | 2012/030593 A2 | 3/2012 |
| WO | WO-2012030593 A3 | 3/2012 |
| WO | WO-2014149266 A2 | 9/2014 |
| WO | WO-2014149266 A3 | 9/2014 |
| WO | WO-2015099684 A1 | 7/2015 |

OTHER PUBLICATIONS

Sadeghi, M. et al. Clinical and Experimental Immunology, 2005, vol. 142, p. 312-317.*
Okamoto, Y. et al. Determination of soluble tumor necrosis factor-alpha receptor type (TNFRI) and II (TNFRII) in the urine of healthy japanese subjects. Journal of Immunoassay and Immunochemistry, 2011, vol. 32, p. 145-155.*
Alford, J. et al. "Cartilage Restoration, Part 1" The American Journal of Sports Medicine, vol. 33, No. 2 (2005) p. 295-306.
Anitua, E et al. "Autologous platelets as a source of proteins for healing and tissue regeneration" Thromb Haemost, vol. 91 (pp. 4-15) 2004.
Anonymous: "Update for veterinarians" Dec. 2012. vet.osu.edu/sites/default/files/documents/pdf/news/vmc/ovmaVeternarianUp/date/20121112.pdf.
Arend, W. et al. "Interleukin-1 Receptor Antagonist: Role in Biology" Annu. Rev. Immunol., vol. 16 (pp. 27-55) 1998.
Baltzer AW, et al. Autologous conditioned serum (Orthokine) is an effective treatment for knee osteoarthritis. Osteoarthritis Cartilage Feb. 1, 2009; 17(2):152-60.
Becker C. et al. Efficacy of epidural perineural injections with autologous conditioned serum for lumbar radicular compression: an Investigator-initiated, prospective, double-blind, reference-controlled study. Spine Aug. 1, 2007; 32 (17):1803-8.
Bendele et al. "Combination benefit of treatment with the cytokine inhibitors interleukin-1 receptor antagonist and PEGylated soluble tumor necrosis factor receptor type I in animal models of rheumatoid arthritis" Arthritis & Rheumatism, vol. 43, No. 12, Dec. 2000, pp. 2648-2659.
Bielecki, T. et al, "Antibacterial effect of autologous platelet gel enriched with growth factors and toher acive substances" J Bone Joint Surg, vol. 89-B, No. 3 (p. 417-420) Mar. 2007.
Bio-Rad Laboratories. Bio-Gel P Polyacrylamide Gel Instruction Manual, Obtained from www.bio-rad.com/webmaster/pdfs/9154_Bio-Gel_P.pdf on Jun. 20, 2012 (14 pages).
Biomet Biologics, Inc. "GPS® II Platelet Concentrate System: The New Gold Standard" Product Brochure (14 pages) Sep. 2006.
Biomet Biologics, Inc. "GPS® III Platelet Separation System" Product Brochure (8 pages) 2007.
Biomet Biologics, Inc. "Plasmax Plasma Concentrate" Product Brochure (6 pages) 2006.
Biomet Biologics, Inc. "Vortech Concentration System Product" Product Brochure (16 pages) Aug. 2005.
Biomet Biologics, Inc. "GPS System Shoulder Recovery with the GPS Platelet Concentrate System" Product Brochure (6 pages) 2004.
Burnouf, T. "Blood-derived, tissue engineering biomaterials" Biomedical Engineering-Applications, Basis & Communications, vol. 16, No. 6, Dec. 2004 (pp. 294-304).
Cell Factor Technologies, Inc. "GPS® Platelet Concentrate System" Product Brochure (9 pages) 2004.
Cell Factor Technologies, Inc., Biomet Europe. "GPS® II System, Gravitational Platelet Separation System" User Manual (13 pages), http://www.cellfactortech.com/global_products.cfm, printed Sep. 16, 2005.
Cell Factor Technologies, Inc., Biomet Europe. "GPS® II System, Gravitational Platelet Separation System, Accelerating the Body's Natural Healing Process" Product Bruchure (16 pages) 2005.
Dallari et al. "Enhanced Tibial Osteotomy Healing with Use of Bone Grafts Supplemented with Platelet Gel or Platelet Gel and Bone Marrow Stromal Cells" The Journal of Bone and Joint Surgery, vol. 89 (2007) pp. 2413-2420.
Dinarello, C. "Interleukin-1 and Interleukin-1 Antagonism" Blood, vol. 77, No. 8 (pp. 1627-1652) Apr. 1991.
Eppley, et al. "Platelet Quantification and Growth Factor Analysis from Platelet-Rich Plasma: Implications for Wound Healing," Plastic and Reconstructive Surgery, 114(6):1502-1508 (Nov. 2004).
Evans, C.H.Novel biological approaches to the intra-articular treatment of osteoarthritis. BioDrugs 2005; 19(6):355-62.
Fiotti et al. "Atherosclerosis and Inflammation. Patterns of Cytokine Regulation in Patients with Peripheral Arterial Disease" Atherosclerosis, Elsevier Ireland Ltd, IE, vol. 145, No. 1, pp. 51-60. Jul. 1, 1999.
Floryan, K. et al. "Home Study Program: Intraoperative use of Autologous Platelet-Rich and Platelet-Poor Plasma for Orthopedic Surgery Patients" vol. 80, No. 4 (Oct. 2004) p. 667-674.
Hou, WH et al. "Microfluidic Devices for Blood Fractionation" Micromachines (2011) 2, 319-343.
Juge-Aubry, C. et al. "Adipose Tissue is a Major Source of Interleukin-1 Receptor Antagonist" Diabetes, vol. 52, May 2003 (pp. 1104-1110).
Kaufman, A. et al. "Human macrophage response to UHMWPE, TiAlV, CoCr, and alumina particles: Analysis of multiple cytokines using protein arrays" Journal of Biomedical Materials Research Part A, published online in Wiley InterScience DOI: 10.1002/jbm.A. 31467 (pp. 464-474) Jul. 2007.
Kim, Seon Hee et al. "Ex vivo gene delivery of Il-1Ra and soluble TNF receptor confers a distal synergistic therapeutic effect in antigen-induced arthritis", Molecular Therapy, vol. 6, No. 5, Nov. 1, 2002 (pp. 591-600).
King, W. et al. "A simple method to Correlate the Concentration of an Anti-Inflammatory Cytokine with White Blood Cells in an Autologous Protein Solution" Feb. 24, 2014.
Klingenberg et al. "Treating inflammation in Atherosclerotic Cardiovascular Disease: Emerging Therapies" European Heart Journal., vol. 30, No. 23, pp. 2838-2844, Dec. 2009.
Lavi, G. et al. "Sustained delivery of IL-1Ra from biodegradable microspheres reduces the number of murine B16 melanoma lung metastases" Journal of Controlled Release. 123, 123-130 (2007).
Lucarelli, E. et al. "Platelet-derived growth factors enhance proliferation of human stromal stem cells" Biomaterials, vol. 24 (2003) pp. 3095-3100.
Matthews, J. et al. "Comparison of the response of primary human peripheral blood mononuclear phagocytes from different donors to challenge with model polyethylene particles of known size and dose" Biomaterials, vol. 21 (pp. 2033-2044) 2000.
Meijer, H. et al. "The production of antiinflammatory cytokines in whole blood by physico-chemical induction" Inflamm. Res., vol. 52 (pp. 404-407) Oct. 2003.
Miltenyi Biotec GmbH, Isolation of Granulocytes From Human Peripheral Blood by Density Gradient Centrifugation (2008) 2 pages.
Morizaki et al. "The Effects of Platelet-Rich Plasma on Bone Marrow Stromal Cell Transplants for Tendon Healing in Vitro" J. Hand Surg. Am., vol. 35, No. 11 (Nov. 2010) pp. 1833-1841.
Murphy et al. "Autologous Bone Marrow Mononuclear Cell Therapy is Safe and Promotes Amputation-free Survival in Patients with Critical Limb Ischemia" Journal of Vascular Surgery, C.V. Mosby Co., vol. 53, No. 6, Jan. 28, 2011.
Muzio, M. et al. "Interleukin-13 Induces the Production of Interleukin-1 Receptor Antagonist (IL-1ra) and the Expression of the mRNA for the Intracellular (Keratinocyte) Form of IL-1ra in Human Myelomonocytic Cells" Blood, vol. 83, No. 7 (pp. 1738-1743) Apr. 1994.
Nursen Düzgün et al. "Cytokine inhibitors: soluble tumor necrosis factor receptor 1 and interleukin-1 receptor antagonist in Behçet's disease" Rheumatology International ; Clinical and Experimental Investigations, Springer, Berlin, DE vol. 25, No. 1, Jan. 2005. p. 1-5.

(56) References Cited

OTHER PUBLICATIONS

O'Shaughnessey, K.M. et al. Blood-derived anti-inflammatory protein solution blocks the effect of IL-1beta on human macrophages in vitro. Inflamm Res Oct. 2011; 60(10):929-36.
Plasmax® Plasma Concentration System. 2007. Biomet Biologics. p. 1-20.
Rader, C. et al."Cytokine Response of Human Macrophage-like Cells After Contact With Polyethylene and Pure Titanium Particles" The Journal of Arthroplasty, vol. 14, No. 7 pp. 840-848 (Oct. 1999).
Sorbera L A "Pegsunercept. Pegylated Soluble Tumor Necrosis Factor Receptor Type 1 PEG-STNF-RI" Drugs of the Future, Prous Science, ES, vol. 28, No. 12. Jan. 1, 2003. p. 1182-1188.
Swift, M. et al. "Characterization of Growth Factors in Platelet Rich Plasma" Cell Factor Technologies, Inc. Printed Sep. 16, 2005 from www.cellfactortech.com/global_products.cfm.
Tateishi-Yuyama, E. et al. "Therapuetic angiogenesis for patients with limb ischaemia by autologous transplantation of bone-barrow cells: a pilot study and randomised controlled trial" The Lancet 2002; 360:427-435.
Ulich, T.R. et al. "Intratrachael Administration of Endotoxin and Cytokines: IV. The Soluble Tumor Necrosis Factor Receptor Type 1 Inhibits Acute Inflammation" American Journal of Pathology; vol. 142, No. 5, May 1993.
Vangsness, T. et al. "Stimulation of IL-1ra Production from Platelet-Rich Plasma" Poster No. 488 presented at 54th Annual Meeting of the Orthopeadic Research Society in San Francisco, CA (1 page) Mar. 2-5, 2008.
Woodell-May, J. et al. "Effect of Incubation Time on Production of IL-1ra and sTNF-RI from Platelet-Rich Plasma" Paper No. 200, 55th Annual Meeting of the Orthopaedic Research Society (1 page) Feb. 2009.
Woodell-May, J. et al. "Elution of IL-1ra from a concentrated-plasma matrix—An in vitro study" Poster Presentation at 8th World Congress of the International Cartilage Repair Society, Miami, FL. (1 page) May 2009.
Woodell-May, J. et al. "Producing Accurate Platelet Counts for Platelet Rich Plasma: Validation of a Hematology Analyzer and Preparation Techniques for Counting" Scientific Foundation, Journal of Carniofacial Surgery, vol. 16, No. 5 (pp. 749-756) Sep. 2005.
Wright-Carpenter, T. "Treatment of Muscle Injuries by Local Administration of Autologous Conditioned Serum: A Pilot Study on Sportsmen with Muscle Strains" Int J Sports Med, vol. 25 (pp. 588-593) Oct. 2004.
Yang, S. et al. "Protective effects of IL-1Ra or vIL-10 gene transfer on a murine model of wear debris-induced osteolysis" Gene Therapy, vol. 11 (pp. 483-491) 2004.
Yang, T. et al. "Recent Applications of Polyacrylamide as Biomaterials" Recent Patents on Materials Science, vol. 1 (pp. 29-40) 2008.
Yoshida S. et al. "Elevation of serum soluble tumour necrosis factor (TNF) receptor and IL-1 receptor antagonist levels in bronchial asthma" Clinical and Experimental Immunology, Wiley-Blackwell Publishing Ltd. vol. 106, No. 1, Oct. 1996.
Zhang et al."IL-1ra alleviates inflammatory hyperalgesia through preventing phosphorylation of NMDA receptor NR-1 subunit in rats" PAIN. vol. 135, No. 3, Mar. 5, 2008, pp. 232-239.
"U.S. Appl. No. 12/394,723, Appeal Brief filed Jun. 15, 2015", 42 pgs.
"U.S. Appl. No. 12/394,723, Decision on Pre-Appeal Brief mailed Feb. 13, 2015", 2 pgs.
"U.S. Appl. No. 12/394,723, Examiner's Answer to Appeal Brief mailed Sep. 9, 2015", 11 pgs.
"U.S. Appl. No. 12/394,723, Final Office Action mailed Apr. 19, 2016", 13 pgs.
"U.S. Appl. No. 12/394,723, Non Final Office Action mailed Oct. 5, 2016", 16 pgs.
"U.S. Appl. No. 12/394,723, Non Final Office Action mailed Dec. 24, 2015", 9 PGS.
"U.S. Appl. No. 12/394,723, Response filed Jan. 8, 2015 to Pre-Appeal Brief Request mailed Dec. 19, 2014", 4 pgs.
"U.S. Appl. No. 12/394,723, Response filed Mar. 24, 2016 to Non Final Office Action mailed Dec. 24, 2015", 18 pgs.
"U.S. Appl. No. 12/394,723, Response filed Aug. 19, 2016 to Final Office Action mailed Apr. 19, 2016", 23 pgs.
"U.S. Appl. No. 12/394,723, Response filed Nov. 9, 2015 to Final Office Action mailed Sep. 8, 2014", 19 pgs.
"U.S. Appl. No. 12/549,116, Decision on Pre-Appeal Brief mailed Feb. 5, 2015", 2 pgs.
"U.S. Appl. No. 12/549,116, Final Office Action mailed Jan. 4, 2016", 15 pgs.
"U.S. Appl. No. 12/549,116, Non Final Office Action mailed Jun. 4, 2015", 12 pgs.
"U.S. Appl. No. 12/549,116, Non Final Office Action mailed Oct. 6, 2016", 15 pgs.
"U.S. Appl. No. 12/549,116, Pre-Appeal Brief Request filed Jan. 8, 2015", 5 pgs.
"U.S. Appl. No. 12/549,116, Response filed Mar. 3, 2016 to Final Office Action mailed Jan. 4, 2016", 11 pgs.
"U.S. Appl. No. 12/549,116, Response filed Sep. 4, 2015 to Non Final Office Action mailed Jun. 4, 2015", 9 pgs.
"U.S. Appl. No. 13/392,266, Final Office Action mailed Jul. 30, 2015", 12 pgs.
"U.S. Appl. No. 13/392,266, Non Final Office Action mailed Feb. 26, 2015", 9 pgs.
"U.S. Appl. No. 13/392,266, Non Final Office Action mailed Oct. 4, 2016", 21 pgs.
"U.S. Appl. No. 13/392,266, Response filed Jan. 22, 2016 to Final Office Action mailed Jul. 30, 2015", 24 pgs.
"U.S. Appl. No. 13/392,266, Response filed Jul. 8, 2015 to Non-Final Office Action mailed Feb. 26, 2015", 13 pgs.
"U.S. Appl. No. 13/782,421, Final Office Action mailed Jan. 15, 2015", 30 pgs.
"U.S. Appl. No. 13/782,421, Notice of Allowance mailed Apr. 27, 2015", 8 pgs.
"U.S. Appl. No. 13/782,421, Response filed Apr. 15, 2015 to Final Office Action mailed Jan. 15, 2015", 6 pgs.
"U.S. Appl. No. 13/837,480, Final Office Action mailed May 23, 2016", 11 pgs.
"U.S. Appl. No. 13/837,480, Non Final Office Action mailed Aug. 11, 2015", 10 pgs.
"U.S. Appl. No. 13/837,480, Non Final Office Action mailed Sep. 13, 2016", 9 pgs.
"U.S. Appl. No. 13/837,480, Response filed Jan. 11, 2016 to Non Final Office Action mailed Aug. 11, 2015", 14 pgs.
"U.S. Appl. No. 13/837,480, Response filed Jul. 25, 2016 to Final Office Action mailed May 23, 2016", 13 pgs.
"U.S. Appl. No. 13/837,480, Response filed Dec. 12, 2016 to Non Final Office Action mailed Sep. 13, 2016", 13 pgs.
"U.S. Appl. No. 13/839,280, Final Office Action mailed Apr. 10, 2015", 17 pgs.
"U.S. Appl. No. 13/839,280, Non Final Office Action mailed Apr. 7, 2016", 16 pgs.
"U.S. Appl. No. 13/839,280, Response filed Aug. 29, 2016 to Non Final Office Action mailed Apr. 7, 2016", 15 pgs.
"U.S. Appl. No. 13/839,280, Response filed Oct. 12, 2015 to Final Office Action mailed Apr. 10, 2015", 9 pgs.
"U.S. Appl. No. 13/840,129, Final Office Action mailed Jun. 18, 2015", 9 pgs.
"U.S. Appl. No. 13/841,083, Final Office Action mailed Sep. 9, 2016", 10 pgs.
"U.S. Appl. No. 13/841,083, Response filed Nov. 29, 2016 to Final Office Action mailed Sep. 9, 2016", 12 pgs.
"U.S. Appl. No. 13/841,103, Final Office Action mailed Aug. 13, 2015", 13 pgs.
"U.S. Appl. No. 13/841,103, Final Office Action mailed Dec. 14, 2016", 24 pgs.
"U.S. Appl. No. 13/841,103, Non Final Office Action mailed Jun. 7, 2016", 16 pgs.
"U.S. Appl. No. 13/841,103, Response filed Jan. 13, 2016 to Final Office Action mailed Aug. 13, 2015", 11 pg.
"U.S. Appl. No. 13/841,103, Response filed Apr. 18, 2016 to Restriction Requirement mailed Feb. 19, 2016", 8 pgs/.

(56) References Cited

OTHER PUBLICATIONS

"U.S. Appl. No. 13/841,103, Response filed May 4, 2015 to Non Final Office Action mailed Dec. 4, 2014", 18 pgs.
"U.S. Appl. No. 13/841,103, Response filed Aug. 31, 2016 to Non Final Office Action mailed Jun. 7, 2016", 15 pgs.
"U.S. Appl. No. 13/841,103, Restriction Requirement mailed Feb. 19, 2016", 7 pgs.
"U.S. Appl. No. 14/050,950, Final Office Action mailed Jun. 17, 2016", 9 pgs.
"U.S. Appl. No. 14/050,950, Non Final Office Action mailed Nov. 19, 2015", 13 pgs.
"U.S. Appl. No. 14/050,950, Notice of Allowance mailed Oct. 6, 2016", 12 pgs.
"U.S. Appl. No. 14/050,950, Response filed Feb. 19, 2016 to Non Final Office Action mailed Nov. 19, 2015", 11 pgs.
"U.S. Appl. No. 14/050,950, Response filed Jun. 23, 2015 to Restriction Requirement mailed Apr. 23, 2015", 1 pgs.
"U.S. Appl. No. 14/050,950, Response filed Aug. 17, 2016 to Final Office Action mailed Jun. 17, 2016", 8 pgs.
"U.S. Appl. No. 14/050,950, Restriction Requirement mailed Apr. 23, 2015", 7 pgs.
"U.S. Appl. No. 14/271,722, Notice of Allowance mailed Jan. 25, 2016", 13 pgs.
"U.S. Appl. No. 14/803,414, Preliminary Amendment filed Sep. 16, 2015", 7 pgs.
"U.S. Appl. No. 14/803,414, Response filed Dec. 19, 2016 to Restriction Requirement mailed Oct. 20, 2016", 7 pgs.
"U.S. Appl. No. 14/803,414, Restriction Requirement mailed Oct. 20, 2016", 7 pgs.
"U.S. Appl. No. 14/803,414, Supplemental Preliminary Amendment Filed Feb. 3, 2016", 8 pgs.
"U.S. Appl. No. 14/808,828, Non Final Office Action mailed Dec. 8, 2016", 10 pgs.
"U.S. Appl. No. 14/808,828, Preliminary Amendment filed Jul. 24, 2015", 12 pgs.
"U.S. Appl. No. 14/808,828, Response filed Oct. 3, 2016 to Restriction Requirement mailed Aug. 2, 2016", 7 pgs.
"U.S. Appl. No. 14/808,828, Restriction Requirement mailed Aug. 2, 2016", 6 pgs.
"U.S. Appl. No. 14/808,828, Supplemental Preliminary Amendment filed Jul. 27, 2015", 10 pgs.
"U.S. Appl. No. 14/808,828, Supplemental Preliminary Amendment filed Oct. 6, 2015", 7 pgs.
"U.S. Appl. No. 14/830,977, Final Office Action mailed Oct. 20, 2016", 12 pgs.
"U.S. Appl. No. 14/830,977, Non Final Office Action mailed Apr. 13, 2016", 16 pgs.
"U.S. Appl. No. 14/830,977, Response filed Jul. 13, 2016 to Non Final Office Action mailed Apr. 13, 2016", 10 pgs.
"U.S. Appl. No. 14/841,086, Examiners Interview Summary mailed Nov. 7, 2016", 3 pgs.
"U.S. Appl. No. 14/973,913, Preliminary Amendment filed Mar. 2, 2016", 10 pgs.
"Arthritis", Mayo Clinic, (Jan. 22, 2013), 1-5.
"Australian Application Serial No. 2011296350, Response filed Jun. 11, 2015 to First Examiner Report mailed Jun. 10, 2014", 20 pgs.
"Canadian Application Serial No. 2,772,067, Office Action railed Jan. 8, 2015", 3 pgs.
"Canadian Application Serial No. 2,772,067, Office Action mailed Nov. 24, 2015", 3 pgs.
"Canadian Application Serial No. 2,772,067, Response filed Mar. 1, 2016 to Office Action mailed Nov. 24, 2015", 7 pgs.
"Canadian Application Serial No. 2,772,067, Response filed Jul. 8, 2015 to Office Action mailed Jan. 8, 2015", 24 pgs.
"Canadian Application Serial No. 2,772,069, Office Action mailed Jul. 20, 2016", 5 pgs.
"Canadian Application Serial No. 2,772,069, Office Action mailed Sep. 16, 2015", 3 pgs.
"Canadian Application Serial No. 2,772,084, Office Action mailed Jun. 11, 2015", 3 pgs.
"Canadian Application Serial No. 2,810,202, Office Action mailed Jul. 2, 2015", 5 pgs.
"Canadian Application Serial No. 2,810,202, Response filed Dec. 30, 2015 to Office Action mailed Jul. 2, 2015", 19 pgs.
"Chinese Application Serial No. 2010800447744, Notification of Reexamination mailed Feb. 23, 2016", W/ English Translation, 9 pgs.
"Chinese Application Serial No. 2010800447744, Response filed Feb. 19, 2015 to Decision on rejection mailed Nov. 15, 2014", W/ English Translation, 13 pgs.
"Chinese Application Serial No. 2010800447744, Response filed Apr. 11, 2016 to Notification of Reexamination mailed Feb. 23, 2016", W/ English Claims, 23 pgs.
"Chinese Application Serial No. 2011800457327, Office Action mailed Mar. 26, 2015", W/ Machine Translation, 18 pgs.
"Chinese Application Serial No. 2011800457327, Office Action mailed Sep. 28, 2015", W/ Machine Translation, 14 pgs pgs.
"Chinese Application Serial No. 2011800457327, Response filed Jun. 10, 2015 to Office Action mailed Mar. 26, 2015", W/ English Claims, 22 pgs.
"Chinese Application Serial No. 201280030026.X, Office Action mailed Nov. 21, 2014", w/ English Translation, 27 pgs.
"Chinese Application Serial No. 201480027178.3, Voluntary Amendment filed Jul. 15, 2016", w/English claims, 35 pgs.
"Chinese Application Serial No. 201480027408.6, Voluntary Amendment mailed Jun. 8, 2016", W/ English Claims, 50 pgs.
"Chinese Application Serial No. 201480027541.1, Voluntary Amendment mailed May 5, 2016", w/ English Claims, 15 pgs.
"European Application Serial No. 10749582.2, Communication Pursuant to Article 94(3) EPC mailed May 10, 2016", 4 pgs.
"European Application Serial No. 10749582.2, Response filed Apr. 16, 2015 to Communication Pursuant to Article 94(3) EPC mailed Dec. 8, 2014", 14 pgs.
"European Application Serial No. 10749582.2, Response filed Aug. 26, 2016 to Communication Pursuant to Article 94(3) EPC mailed May 10, 2016", 13 pgs.
"European Application Serial No. 10754379.5, Response filed Apr. 13, 2015 to Examination Notification Art. 94(3) mailed Dec. 15, 2014", 8 pgs.
"European Application Serial No. 10754613.7, Communication Pursuant to Article 94(3) EPC mailed Nov. 13, 2015", 4 pgs.
"European Application Serial No. 10754613.7, Response filed Mar. 15, 2016 to Communication Pursuant to Article 94(3) EPC mailed Nov. 13, 2015", 26 pgs.
"European Application Serial No. 11754786.9, Grounds for the decision mailed Oct. 13, 2015", 7 pgs.
"European Application Serial No. 11754786.9, Response filed Feb. 6, 2015 to Communication Pursuant to Article 94(3) EPC mailed Oct. 8, 2014", 9 pgs.
"European Application Serial No. 11754786.9, Summons to Attend Oral Proceedings mailed Mar. 10, 2015", 3 pgs.
"European Application Serial No. 13165543.3, Response filed Oct. 24, 2014 to Non Final Office Action mailed Jun. 27, 2014", 6 pgs.
"European Application Serial No. 14707069.2, Communication Pursuant to Article 94(3) EPC mailed Nov. 15, 2016", 7 pgs.
"European Application Serial No. 14707069.2, Response filed May 23, 2016 to Communication pursuant to Rules 161(1) and 162 EPC mailed Nov. 12, 2015", 12 pgs.
"European Application Serial No. 14707909.9, Communication Pursuant to Article 94(3) EPC mailed Jul. 22, 2016", 9 pgs.
"European Application Serial No. 14707909.9, Preliminary Amendment filed on May 13, 2016", 14 pgs.
"European Application Serial No. 14707909.9, Response filed Dec. 6, 2016 to Communication Pursuant to Article 94(3) EPC mailed Jul. 22, 2016", 11 pgs.
"European Application Serial No. 14709014.6, Communication Pursuant o Article 94(3) EPC mailed Oct. 20, 2016", 12 pgs.
"European Application Serial No. 14709014.6, Office Action mailed Nov. 19, 2015", 2 pgs.
"European Application Serial No. 14709014.6, Response filed May 27, 2016 to Office Action mailed Nov. 19, 2015", 15 pgs.

(56) References Cited

OTHER PUBLICATIONS

"European Application Serial No. 14709803.2, Response filed May 16, 2016 to Communication pursuant to Rules 161(1) and 162 EPC mailed Nov. 5, 2015", 14 pgs.
"European Application Serial No. 14714491.9, Response filed Aug. 1, 2016 to Communication Pursuant to Rules 161 and 162 EPC mailed Jan. 21, 2016", 11 pgs.
"European Application Serial No. 14724817.3, Office Action mailed Oct. 27, 2015", 2 pgs.
"European Application Serial No. 14724817.3, Response filed May 6, 2016 to Communication pursuant to Rules 161(1) and 162 EPC mailed Oct. 27, 2015", 13 pgs.
"European Application Serial No. 14729994.5, Response filed May 9, 2016 to Communication pursuant to Rules 161(1) and 162 EPC mailed Oct. 30, 2015", 14 pgs.
"European Application Serial No. 15184504.7, Communication Pursuant to Article 94(3) EPC mailed Sep. 16, 2016", 5 pgs.
"European Application Serial No. 15184504.7, Extended European Search Report mailed Oct. 20, 2015", 7 pgs.
"International Application Serial No. PCT/US2013/056793, International Preliminary Report on Patentability mailed Mar. 12, 2015", 8 pgs.
"International Application Serial No. PCT/US2014/016421, International Preliminary Report on Patentability mailed Sep. 24, 2015", 16 pgs.
"International Application Serial No. PCT/US2014/021707, International Preliminary Report on Patentability mailed Sep. 24, 2015", 16 pgs.
"International Application Serial No. PCT/US2014/023091, International Preliminary Report on Patentability mailed Sep. 24, 2015", 11 pgs.
"International Application Serial No. PCT/US2014/028942, International Preliminary Report on Patentability mailed Sep. 24, 2015", 15 pgs.
"Japanese Application Serial No. 2012-526990, Examiners Decision of Final Refusal mailed Jun. 3, 2016", W/ English Translation, 6 pgs.
"Japanese Application Serial No. 2012-526990, Office Action mailed Jun. 26, 2015",W/ English Translation, 12 pgs.
"Japanese Application Serial No. 2012-526990, Response filed Dec. 25, 2015 to Office Action mailed Jun. 26, 2015", W/ English Translation, 14 pgs.
"Japanese Application Serial No. 2012-527030, Office Action mailed Jun. 12, 2015", W/ English Translation, 2 pgs.
"Japanese Application Serial No. 2013-174962, Notice of Reasons for Rejection mailed Jul. 31, 2015", W/ English Translation, 10 pgs.
"Japanese Application Serial No. 2013-174962, Response filed Mar. 12, 2015 to Office Action mailed Sep. 12, 2014", W/ English Translation, 18 pgs.
"Japanese Application Serial No. 2013-174962, Response filed Oct. 30, 2015 to Notice of Reasons for Rejection mailed Jul. 31, 2015", W/ English Claims, 16 pgs.
"Japanese Application Serial No. 2013-527119, Examiners Decision of Final Refusal mailed Oct. 18, 2016", W/ English Translation, 9 pgs.
"Japanese Application Serial No. 2013-527119, Office Action mailed Mar. 1, 2016", W/ English Translation, 12 pgs.
"Japanese Application Serial No. 2013-527119, Office Action mailed Jun. 12, 2015" W/ English Translation, 11 pgs.
"Japanese Application Serial No. 2013-527119, Response filed Aug. 1, 2016 to Office Action mailed Mar. 1, 2016", W/ English Claims, 13 pgs.
"Japanese Application Serial No. 2013-527119, Response filed Oct. 1, 2015 to Office Action mailed Jun. 12, 2015", W/ English Claims, 12 pgs.
"Japanese Application Serial No. 2014-024420, Preliminary Notice of Reasons for Rejection mailed Feb. 24, 2015", w/ English Translation, 15 pgs.
"Mexican Application Serial No. Mxa2013002488, Office Action mailed Nov. 5, 2015", W/ English Translation, 7 pgs.

Andia, Isabel, et al., "Platelet-rich plasma for managing pain and inflammation in osteoarthritis", Nature Reviews Rheumatology, vol. 9. No. 12., (Oct. 1, 2013), 721-730.
Belal, Mahmoud Helmy, "Recombinant Human Platelet-Derived Growth Factor-BB: a promising role for fibroblast cell attachment in chronic periodontitis. A concentration-dependent effect on human cell adhesion: SEM study", Rev. Clin. Pesq. Odontol., Curitiba, v. 5, n. 3, (2009), p. 225-240.
Clayden, J D, et al., "Improved segmentation reproducibility in group tractography using a quantitative tract similarity measure", Neuroimage, Academic Press, Orlando, FL, US vol. 33, No. 2, (Nov. 1, 2006), 482-492.
Dayer, Jean-Michel, et al., "Adipose tissue has anti-inflammatory properties: focus on IL-1 receptor antagonist (IL-1Ra)" Annals of the New York Academy of Sciences, vol. 1069, (Jun. 2006), 444-53.
Ehricke, H H, et al., "Visualizing MR diffusion tensor fields by dynamic fiber tracking and uncertainty mapping", Computers and Graphics, Elsevvier vol. 30, No. 2, (Apr. 1, 2006), 255-264.
Fini, et al., "Effects of pulsed electromagnetic fields on articular hyaline cartilage: review of experimental and clinical studies", Biomedicine and Pharmacotherapy, Elsevier, FR, vol. 59, No. 7, (Aug. 1, 2005), 388-394.
Honore, Prisca, et al., "Interleukin-1aB gene-deficient mice show reduced nociceptive sensitivity in models of inflammatory and neuropathic pain but not post-operative pain", Behavioral Brain Research, (2006), 355-364.
Jones, D K, et al., "Confidence mapping in diffusion ensor magnetic resonance imaging tractography using a bootstrap approach", Magnetic Resonance in Medicine Wiley USA, vol. 53 , No. 5, (May 2005), 1143-1149.
Kohsaka, Hitoshi, "Gene Transfer Therapy for Rheumatoid Arthritis", Japanese Journal of Clinical Medicine, No. 63, No. 9, (2005), 8 pgs.
Kwon, Young-Bae, et al., "Topical application of epidermal growth factor accelerates wound healing by myofibroblast proliferation and collagen synthesis in rat", Journal of Vetrinary Science 7(2), (2006), 105-109 pgs.
Laplante, Ben L, et al., "Spine osteoarthritis", PM&R, vol. 4, (2012), 528-536.
Lori, N F, et al., "Diffusion tensor fiber tracking of human brain connectivity: acquisition methods, reliability analysis and biological results", NMR in Biomedicine Wiley UK, vol. 15, No. 7-8, (Nov. 2002), 493-515.
Matuska, et al., "Autologous Solution Protects Bovine Cartilage Explants from IL-1a and STFa-Induced Cartilage Degradation", Journal of Orthopaedic Research, (Jul. 16, 2013), 7 pgs.
Nalamachu, Srinivas, "An Overview of Pain Management: The Clinical Efficacy and Value of Treatment", Am. J. Manag. Care. 19, (2013), 261-266.
Parchment, et al., "Roles for in vitro myelotoxicity tests in preclincial drug development and clinical trial planning, Toxicology Pathology, Society of Toxicological Pathologists", vol. 21, No. 2, (1993), 241-250.
Pommer, et al., "Dielectrophoretic separation of platelets from whole blood in microfluidic channels", Electrophoresis, (2008), 1213-1218.
Re, Fabio, et al., "Expression of interleukin-1 receptor antagonist (IL-ra) by human circulating polymorphonuclear cells", European Journal of Immunology, 23, (1993), 570-573 pgs.
Sarzi-Puttini, Piercarlo, et al., "The Appropriate Treatment of Chronic Pain", Clin. Drug Investig. 32, (2012), 21-33.
Shiozawa, Kazuko, et al., "Gene Therapy, Is a total therapy for rheumatoid arthritis possible?", Pharma Medica, vol. 17, No. 10 w/ partial English Translation, (1999), 16 pgs.
Shrivastava, Abha, et al, "Effects of Electromagnetic Forces Of Earth On Human Biological System", Indian J. Prey. Soc. Med, Retrieved from the Internet: <URL:http://medind.nic.in/ibl/t09/i3/iblt09i3p162.pdf>, (Jan. 1, 2009), 162-167.
Shu-Li, Lin, et al., "Static magnetic field attenuates mortality rate of mice by increasing the production of IL-1 receptor antagonist", Int. J. Radiat. Biol. 2009, 85(7), (Jul. 31, 2009), 633-640.

(56) References Cited

OTHER PUBLICATIONS

Tiaka, Elisavet K., et al., "Epidermal Growth Factor in the Treatment of Diabetic Foot Ulcers: An Update", Perspectives in Vascular Surgery and Endovascular Therapy 24(1), (2012), p. 37-44.
Wang, "Cell separation by dielectrophoretic field-flow-fractionation", Analytical Chemistry, (2000), 832-839.
Younger, Jarred, et al., "Pain Outcomes: A Brief Review of Instruments and Techniques", Curr Pain Headache Rep. 13(1), (Feb. 2009), p. 39-43.
"A phase I safety study of combination treatment with pegylated soluble tumor necrosis factor receptor type I (PET STNF-RI) and anakinra (interleukin-1 receptor antagonist, IL-1RA) in patients with rheumatoid arthritis", Prous integrity, (Jun. 12, 2002), 1-1.
"U.S. Appl. No. 13/840,562, Final Office Action mailed Jan. 20, 2016", 14 pgs.
"U.S. Appl. No. 13/840,562, Non Final Office Action mailed Apr. 24, 2015", 23 pgs.
"U.S. Appl. No. 13/840,562, Response filed Apr. 18, 2016 to Final Office Action mailed Jan. 20, 2016", 18 pgs.
"U.S. Appl. No. 13/840,562, Response filed Jul. 29, 2015 to Non Final Office Action mailed Apr. 24, 2015", 13 pgs.
"U.S. Appl. No. 13/841,083, Examiner Summary Received Jan. 29, 2016", 1 pg.
"U.S. Appl. No. 13/841,083, Non Final Office Action mailed Jan. 29, 2016", 11 pgs.
"U.S. Appl. No. 13/841,083, Non Final Office Action mailed Jul. 15, 2015", 8 pgs.
"U.S. Appl. No. 13/841,083, Response filed Apr. 10, 2015 to Non Final Office Action mailed Dec. 10, 2014", 17 pgs.
"U.S. Appl. No. 13/841,083, Response filed Apr. 28, 2016 to Non Final Office Action mailed Jan. 29, 2016", 11 pgs.
"U.S. Appl. No. 13/841,083, Response filed Aug. 27, 2014 to Restriction Requirement mailed Jul. 21, 2014", 3 pgs.
"U.S. Appl. No. 13/841,083, Response filed Oct. 13, 2015 to Non Final Office Action mailed Jul. 15, 2015", 10 pgs.
"Arthritis", [Online]. Retrieved from the Internet: Wayback Machine <URL:http://www.mayoclinic.org/diseases-conditions/arthritis/basics/treatment/con-20034095 >, (2014), 5 pgs.
"Canadian Application Serial No. 2,905,552, Voluntary Amendment filed Sep. 11, 2015".
"Canadian Application Serial No. 2,906,310, Voluntary Amendment filed Sep. 14, 2015", 2 pgs.
"International Application Serial No. PCT/US2014/016384, International Preliminary Report on Patentability mailed Sep. 24, 2015", 16 pgs.
"International Application Serial No. PCT/US2014/016384, International Search Report mailed Oct. 9, 2014", 10 pgs.
"international Application Serial No. PCT/US2014/016384, Written Opinion mailed Oct. 9, 2014", 14 pgs.
"International Application Serial No. PCT/US2014/016895, International Preliminary Report on Patentability mailed Sep. 24, 2015", 16 pgs.
"International Application Serial No. PCT/US2014/016900, International Preliminary Report on Patentability mailed Sep. 24, 2015", 9 pgs.
Bendele, Alison M, et al., "Combination Benefit Of Treatment With The Cytokine Inhibitors Interleukin-1 Receptor Antagonist And Pegylated Soluble Tumor Necrosis Factor Receptor Type I In Animal Models Of Rheumatoid Arthritis", Arthritis & Rheumatism, J.B. Lippincott vol. 43, No. 12, (Dec. 1, 2000), 2648-2659.
Carpenter, et al., "Rationale Design of stable protein formulations—theory and practice", Rationale design of stable lyophilized protein formulations: theory and practice,, (2002), 109-133.
Dawson, J, et al., "Effects of soluble interleukin-1 type II receptor on rabbit antigen-induced arthritis: Clinical, biochemical and histological assessment", Rheumatology (Oxford) vol. 38, No. 5, (May 5, 1999), 401-406.
Kimble, Robert B, et al., "Simultaneous block of interleukin-1 and tumor necrosis factor is required to completely prevent bone loss in the early postovariectomy period", Endocrinology, The Endocrine Society, US, vol. 136, No. 7—Abstract, (Jul. 1, 1995), 1 pg.
Kitazawa, R, et al., "Interleukin-1 Receptor Antagonist And Tumor Necrosis Factor Binding Protein Decrease Osteoclast Formation And Bone Resorption In Ovariectornized Mice", Journal Of Clinical Investigation, American Society for Clinical Investigation, US, vol. 94, No. 6, (Dec. 1, 1994), 2397-2406.
Mehta, Sanjay, et al., "Gentamicin distribution from a collagen carrier", Journal Of Orthopaedic Research, vol. 14, No. 5—Abstract, (Sep. 1, 1996), 749-754.
Okunishi, K, et al., "Hepatocyte Growth Factor Significantly Suppresses Collagen-Induced Arthritis in Mice", The Journal of Immunology, vol. 179, No. 8, (Oct. 15, 2007), 15 pgs.
Sevenoaks, Martin J., et al., "Chronic Obstructive Pulmonary Disease, inflammation and co-morbidity—a common inflammatory phenotype?", respiratory Research vol. 7:70, (2006), 1-9.
Solchaga, Luis A., et al., "Hyaluronic Acid-Based Polymers As Cell Carriers For Tissue-Engineered Repair Of Bone And Cartilage", Journal Of Orthopaedic Research, Orthopaedic Research Society, US, vol. 17, (Jan. 1, 1999), 205-213.
Ulich, et al., "Intratracheal Administration of Endotoxin and Cytokines: IV. The Soluble Tumor Necrosis Factor Receptor Type 1 Inhibits Acute Inflammation", American Journal of Pathology; [10640], Elsevier Inc, US, vol. 142, No. 5, (May 1, 1993), 1335-1338.

* cited by examiner

ACELLULAR COMPOSITIONS FOR TREATING INFLAMMATORY DISORDERS

INTRODUCTION

The present technology relates to methods of treating inflammatory disorders, including osteoarthritis. In particular, methods comprise use of acellular solutions comprising cytokines.

Inflammation is a complex cellular and biochemical process that occurs in the affected blood vessels and adjacent tissues in response to an injury or abnormal stimulation caused by a physical, chemical, or biologic agent, such as a pathogen, allergen or irritant. The inflammatory process includes local reactions and resulting morphologic changes in tissue; the destruction or removal of the causative agent; and the responses that lead to repair and healing. In most instances, inflammation is a beneficial and transient process, which subsides as the body attacks and overcomes an infectious or other harmful agent. However, in some instances, inflammation can be chronic self-perpetuating process, for example, as part of an ongoing degenerative process (such as arthritis) or autoimmune disease, leading to destruction of tissue. Chronic inflammation is associated with a variety of disorders, including rheumatoid arthritis, atherosclerosis, ischemic heart disease, periodontitis, colitis, and some cancers.

An inflammatory response consists of a cascade of biochemical events, involving the local vascular system and immune system, and various cells within the injured tissue. The process involves the release of numerous cell-derived mediators, including histamine, interferon-gamma, interleukin-8, leukotriene, nitric oxide, prostaglandins, tumor necrosis factor-alpha, and interleukin-1. In particular, interleukin-1 (IL-1) includes a family of cytokines that can stimulate lymphocytes and macrophages, activate phagocytes, increase prostaglandin production, contribute to degeneration of bone joints, increase bone marrow cell proliferation, and are involved in many chronic inflammatory conditions. IL-1 can be generated by macrophages, monocytes, and dendritic cells, and can be part of the inflammatory response against infection.

The mode of action of IL-1 can be mediated by interleukin-1 receptor antagonist protein (IL-1ra; also known as "IRAP"). IL-1ra binds to the same receptor on the cell surface as IL-1, and thus prevents IL-1 from sending a signal to that cell. IL-1ra is secreted from white blood cells, including monocytes, macrophages, neutrophils, polymorphonuclear cells (PMNs), and other cells, and can modulate a variety of IL-1 related immune and inflammatory responses, as described by Arend W P, Malyak M, Guthridge C J, Gabay C (1998) "Interleukin-1 receptor antagonist: role in biology" Annu. Rev. Immunol. 16: 27-55. Production of IL-1ra is stimulated by several substances including adherent immunoglobulin G (IgG), other cytokines, and bacterial or viral components. IL-1ra, as well as other cytokines such as soluble tumor necrosis factor receptor 1 (sTNF-R1), soluble tumor necrosis factor receptor 2 (sTNF-R2) and (soluble interleukin receptor II (sIL-1RII), is an important natural anti-inflammatory protein in arthritis, colitis, and granulomatous pulmonary disease.

IL-1ra can be used in the treatment of rheumatoid arthritis, an autoimmune disease in which IL-1 plays a key role, reducing inflammation and cartilage degradation associated with the disease. For example, Kineret™ (anakinra) is a recombinant, non-glycosylated form of IL-1ra (Amgen Manufacturing, Ltd., Thousand Oaks, Calif.). Various recombinant interleukin-1 inhibitors and methods of treatment are described in U.S. Pat. No. 6,599,873, Sommer et al., issued Jul. 29, 2003; U.S. Pat. No. 5,075,222, Hannum et al., issued Dec. 24, 1991; and U.S. Application Publication No. 2005/0197293, Mellis et al., published Sep. 8, 2005 In addition, methods for producing IL-1ra from body fluids, including the use of autologous fluids, are described in U.S. Pat. No. 6,623,472, Reinecke et al., issued Sep. 23, 2003; U.S. Pat. No. 6,713,246, Reinecke et al., issued Mar. 30, 2004; and U.S. Pat. No. 6,759,188, Reinecke et al., issued Jul. 6, 2004.

Many such treatments for inflammation are known in the art. Therapies known in the art may be directed to removal of the underlying irritant or agent causing the inflammatory reaction, or by mediating one or more aspects of the inflammatory response. Examples include glucocorticoid steroids (such as hydrocortisone, cortisone, prednisone, and beclomethasone), non-steroidal anti-inflammatory drugs (such as aspirin, ibuprofen and naproxen), and immune selective anti-inflammatories. However, many such treatments present side effects, particularly during chronic administration, or have pharmacologic characteristics that limit their use. For example, while compositions and methods using IL-1ra are known in the art, they may be associated with issues regarding stability and half-life of IL-1ra as well as the amount and rate of IL-1ra provided. Moreover, many treatments do nothing to address the underlying causes of the inflammatory process. Accordingly, improved methods of treating inflammation are needed, offering one or more of improved efficacy, reduced side effects, and improved dosing characteristics.

SUMMARY

The present technology provides methods for generating acellular compositions comprising anti-inflammatory cytokines for use in treatment of inflammation and other disorders mediated by interleukin-1 and tumor necrosis factor-alpha. Such compositions comprise the following components:

(a) interleukin-1 receptor antagonist (IL-1ra); and (b) soluble tumor necrosis factor receptor I (sTNF-r1);

wherein at least one of the components is derived from urine, clotted blood, or tissue culture. In various embodiments, the IL-1ra has a concentration of at least about 10,000 pg/ml, and the sTNF-RI has a concentration of at least about 1,200 pg/ml. The composition may further comprise soluble tumor necrosis factor receptors II (sTNF-RII), platelet derived growth factors AB and BB (PDGF-AB and PDGF-BB), epidermal growth factor (EGF), and mixtures thereof. In some embodiments, the composition further comprises at least one of hepatocyte growth factor (HGF) or soluble interleukin-1 receptor II (sIL-1RII).

Methods for producing compositions are also provided, including methods for making an acellular composition for the treatment of a disorder mediated by IL-1 comprising:

(a) culturing, in a growth medium, cells that produce IL-1ra and, optionally, other cytokines such as tumor necrosis factor-alpha;

(b) isolating the medium; and (c) freeze drying the composition.

Culturing may be performed in a monolayer culture, a bioreactor, or a non-adherent culture, using cultured cells that are genetically engineered to overproduce IL-1ra. Methods may also comprise subjecting the cells to an electromagnetic field. Components of the acellular compositions may also be derived from biologic materials, such as blood clots and urine.

Figure 1:
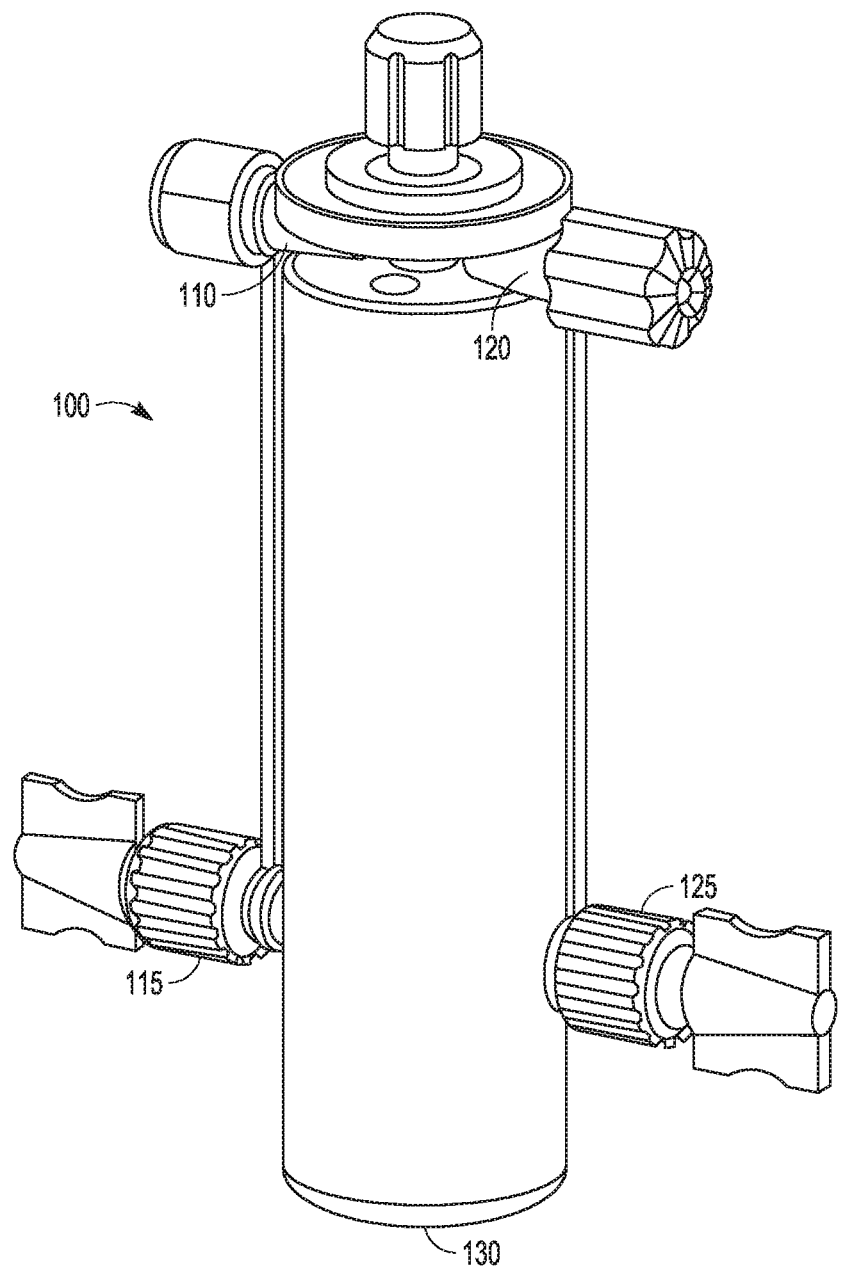
FIG. 1 is a diagram of a device for generating a blood clot.

Corresponding reference numerals indicate corresponding parts throughout the several views of the drawings. It should be noted that the figures set forth herein are intended to exemplify the general characteristics of materials, compositions, devices, and methods among those of the present technology, for the purpose of the description of certain embodiments. These figures may not precisely reflect the characteristics of any given embodiment, and are not necessarily intended to fully define or limit specific embodiments within the scope of this technology.

DESCRIPTION

The following description of technology is merely exemplary in nature of the composition, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The present technology relates to compositions, methods of making compositions, and methods of using compositions for the treatment of inflammatory disorders, and other disorders mediated by interleukin-1. Compositions comprise two or more cytokines, at least one of which is derived from urine, clotted blood or tissue culture.

Protein Compositions

The present technology provides methods for treating inflammatory disorders other disorders mediated by interleukin-1 in humans or other mammalian subjects using compositions (herein referred to as "Protein Solutions") comprising proteins dissolved, suspended or otherwise carried for delivery to a mammalian subject in a physiologically-acceptable medium. In various embodiments, such compositions comprise proteins (e.g., cytokines) that are native to whole blood in normal mammal subjects.

Compositions of this technology are acellular. Such "acellular" compositions contain no, or are essentially free of, viable white blood cells, platelets, or other cells. Preferably, while compositions may contain proteins derived from cells, the compositions do not contain cellular fragments that are capable of creating an immunogenic response in a mammalian subject.

In various embodiments, the Protein Solution comprises at least two proteins selected from the group consisting of IL-1ra, sTNF-RI, sTNF-RII (soluble tumor necrosis factor-receptor 2), IGF-I (insulin-like growth factor 1), EGF (epidermal growth factor), HGF (hepatocyte growth factor), PDGF-AB (platelet-derived growth factor AB), PDGF-BB (platelet-derived growth factor BB), VEGF (vascular endothelial growth factor), TGF-β1 (transforming growth factor-β1, and sIL-1RII (soluble interleukin receptor II), wherein the concentration of each protein in the composition is greater than the concentration of the protein in normal blood. For the sake of clarity, the Protein Solution may contain three or more of the proteins from the recited group. While the concentration of every such protein in the composition may be greater than its respective concentrations in normal blood, it is not necessary that the concentration of more than two of the proteins be greater than their respective concentrations in normal blood.

In various embodiments, the protein solution comprises the following components.

TABLE 1

Protein Solution Exemplary Components

| Component | Composition Concentration | Normal Whole Blood Concentration |
|---|---|---|
| IL-1ra | about 10,000 pg/ml or greater about 25,000 pg/ml or greater about 30,000 pg/ml or greater from about 25,000 to about 110,000 pg/ml from about 25,000 to about 40,000 pg/ml | about 4200 pg/ml |
| sTNF-RI | about 1,200 pg/ml or greater about 1,800 pg/ml or greater about 3,000 pg/ml or greater | about 630 pg/ml |
| sTNF-RII | about 3,000 pg/ml or greater about 5,000 pg/ml or greater about 7,000 pg/ml or greater about 9,000 pg/ml or greater | about 1200 pg/ml |
| sIL-1RII | about 15,000 pg/ml or greater about 20,000 pg/ml or greater about 25,000 pg/ml or greater | about 11,800 pg/ml |
| Growth factors | | |
| EGF | about 800 pg/ml or greater about 1,000 pg/ml or greater about 1,200 pg/ml or greater | about 250 pg/ml |
| HGF | about 1,000 pg/ml or greater about 2,500 pg/ml or greater about 2,800 pg/ml or greater about 3,000 pg/ml or greater | about 500 pg/ml |
| PDGF-AB | about 35,000 pg/ml or greater about 50,000 pg/ml or greater about 70,000 pg/ml or greater | about 6,000 pg/ml |
| PDGF-BB | about 10,000 pg/ml or greater about 15,000 pg/ml or greater about 20,000 pg/ml or greater | about 1,500 pg/ml |
| TGF-β1 | about 100,000 pg/ml or greater about 150,000 pg/ml or greater about 190,000 pg/ml or greater | about 10,000 pg/ml |
| IGF-1 | about 130,000 pg/ml or greater about 150,000 pg/ml or greater about 160,000 pg/ml or greater | about 70,000 pg/ml |
| VEGF | about 500 pg/ml or greater about 600 pg/ml or greater about 800 pg/ml or greater | about 150 pg/ml |
| Component | | |
| IL-1ra | about 10,000 pg/ml or greater about 25,000 pg/ml or greater about 30,000 pg/ml or greater from about 25,000 to about 110,000 pg/ml from about 25,000 to about 40,000 pg/ml | about 8100 pg/ml |
| sTNF-RI | about 1,200 pg/ml or greater about 1,800 pg/ml or greater about 3,000 pg/ml or greater | about 630 pg/ml |
| sTNF-RII | about 5,000 pg/ml or greater about 7,000 pg/ml or greater about 9,000 pg/ml or greater | about 2500 pg/ml |
| sIL-1RII | about 15,000 pg/ml or greater about 20,000 pg/ml or greater about 25,000 pg/ml or greater | about 11,800 pg/ml |

TABLE 1-continued

Protein Solution Exemplary Components

| | Composition Concentration | Normal Whole Blood Concentration |
|---|---|---|
| Growth factors | | |
| EGF | about 800 pg/ml or greater<br>about 1,000 pg/ml or greater<br>about 1,200 pg/ml or greater | about 250 pg/ml |
| HGF | about 2,500 pg/ml or greater<br>about 2,800 pg/ml or greater<br>about 3,000 pg/ml or greater | about 800 pg/ml |
| PDGF-AB | about 35,000 pg/ml or greater<br>about 50,000 pg/ml or greater<br>about 70,000 pg/ml or greater | about 24,000 pg/ml |
| PDGF-BB | about 10,000 pg/ml or greater<br>about 15,000 pg/ml or greater<br>about 20,000 pg/ml or greater | about 4,700 pg/ml |
| TGF-β1 | about 100,000 pg/ml or greater<br>about 150,000 pg/ml or greater<br>about 190,000 pg/ml or greater | about 55 pg/ml |
| IGF-1 | about 130,000 pg/ml or greater<br>about 150,000 pg/ml or greater<br>about 160,000 pg/ml or greater | about 115,000 pg/ml |
| VEGF | about 500 pg/ml or greater<br>about 600 pg/ml or greater<br>about 800 pg/ml or greater | about 370 pg/ml |

Protein concentrations can be measured using the methods known in the art. For example, Quantikine Human Immunoassays (R&D Systems, Inc., Minneapolis, Minn.) may be used to assay for IL-1ra, IL-1β, IL-8, sTNF-RI, TNF-α, IL-6, sTNF-RII, IL-10, IL-13, and IL-4, according to the manufacturer's instructions. Immunoassays may performed for hepatocyte growth factor and soluble IL-1RII.

In various embodiments, the concentration of one or more of the proteins or other components in the Protein Solution is greater than the concentration of the component in normal blood. (Compositions with such higher concentrations of components are said to be "rich" in such components.) As referred to herein, the concentration of a component in "normal" blood or other tissue is the concentration found in the general population of mammalian subjects, e.g., in normal whole blood. It will be understood that this concentration is species specific.

Thus, in various embodiments, the concentration of one or more components of the Protein Solution is greater than about 1.5 times, about 2 times, or about 3 times, greater than the concentration of the component in normal blood. For example, components may have greater concentrations in the compositions, relative to normal (whole) blood, as follows:

IL-1ra, at a concentration that is at least about 2.5, or at least about 3 or at least about 5, times greater;
sTNF-RI, at a concentration that is at least about 2, or at least about 2.5 or at least about 3, times greater;
sTNF-RII, at a concentration that is at least about 2, or at least about 2.5 or at least about 3, times greater;
sIL-1RII, at a concentration that is at least about 1.5, or at least about 1.8 or at least about 2, times greater;
EGF, at a concentration that is at least about 2, or at least about 3 or at least about 5, times greater;
HGF, at a concentration that is at least about 2, or at least about 3 or at least about 4, times greater;
PDGF-AB, at a concentration that is at least about 2, or at least about 3 or at least about 5, times greater;
PDGF-BB, at a concentration that is at least about 2, or at least about 3 or at least about 5, times greater;
TGF-β1, at a concentration that is at least about 3, or at least about 4 or at least about 6, times greater;
IGF-1, at a concentration that is at least about 1.2, or at least about 1.4 or at least about 1.5, times greater; and
VEGF, at a concentration that is at least about 2, or at least about 2.5 or at least about 3, times greater.

For example, a Protein Solution may comprise:
(a) at least about 10,000 pg/ml IL1-ra;
(b) at least about 1,200 pg/ml sTNF-RI; and
(c) a protein selected from the group consisting of sTNF-RII, IGF-I, EGF, HGF, PDGF-AB, PDGF-BB, VEGF, TGF-β1, and sIL-1RII, and mixtures thereof, wherein the protein has a concentration higher than the protein's baseline concentration in normal blood. In another example, a Protein Solution comprises:
(a) interleukin-1 receptor antagonist (IL-1ra), at a concentration of from at least 3 times greater than the concentration of IL-1ra in normal blood;
(b) soluble tissue necrosis factor-r1 (sTNF-r1), at a concentration at least 2 times greater than the concentration of IL-1ra in normal blood.

Methods of Making Protein Solutions

Protein Solutions may be made by any of a variety of methods, including admixture of individual components and processes wherein one or more components are derived from a source material. In various embodiments, the Protein Solution is made by admixture of components obtained from natural or synthetic sources. Without limiting the scope, mechanism or function of the present technology, such acellular anti-inflammatory cytokine compositions may offer advantages in certain applications, insofar as they may not create an immunogenic response in subjects to whom they are administered.

In particular, by way of example, a Protein Solution may comprise interleukin-1 receptor antagonist (IL-1ra) that is synthetic or recombinant, or isolated from autologous, allogeneic or xenogeneic blood or other biologic sources, aside from the methods described above. For example, Kineret™ (anakinra) is a recombinant, non-glycosylated form of IL-1ra, sold by Amgen Manufacturing, Ltd. (Thousand Oaks, Calif.). Various recombinant interleukin-1 inhibitors and methods of treatment are described in U.S. Pat. No. 6,599,873, Sommer et al., issued Jul. 29, 2003; U.S. Pat. No. 5,075,222, Hannum et al., issued Dec. 24, 1991; and U.S. Application Publication No. 2005/0197293, Mellis et al., published Sep. 8, 2005. In addition, methods for producing IL-1ra from body fluids, including the use of autologous fluids, are described in U.S. Pat. No. 6,623,472, Reinecke et al., issued Sep. 23, 2003; U.S. Pat. No. 6,713,246, Reinecke et al., issued Mar. 30, 2004; and U.S. Pat. No. 6,759,188, Reinecke et al., issued Jul. 6, 2004. When an allogeneic anti-inflammatory cytokine composition is to be generated, multiple sources of IL-1ra from multiple subjects may be pooled together.

Components of the acellular Protein Solutions may also be derived from biologic materials, such as blood clots and urine. Components may also be obtained from cell cultures.

Obtaining Components from Blood Clots

In particular, methods include obtaining one or more Protein Solution components from a liquid ("clot extract") trapped in a blood clot. A liquid (cell releasate) can be obtained by compression ("squeezing"), clot disruption, or centrifugation. Blood useful in making clots may be autologous (i.e., obtained from the subject to be treated using the Protein Solution) or from allogeneic sources (i.e., from subjects of the same species as the subject to whom the solution is to be administered) or xenogeneic sources (i.e., from animal sources other than the species to whom the solution is to be administered). In some embodiments, allogeneic blood is obtained from a plurality of donors.

The blood clot can be made with or without anticoagulant and with or without exogenous thrombin by combining blood or a blood fraction with a clotting agent. Suitable clotting agents include thrombin (e.g., bovine, recombinant human, pooled human, or autologous), autologous clotting protein, and polyethylene glycol. Calcium may be in the form of a calcium salt, such as calcium chloride.

In some embodiments, the clotting agent comprises a clotting protein. A suitable clotting fraction can be obtained by a process of: loading whole blood or plasma with a calcium solution (e.g., calcium chloride in ethanol) into a blood isolation device; heating the whole blood or plasma for at least about 20 minutes, at a temperature of at least about 20° C.; and isolating the clotting fraction. The isolating may be performed by centrifuging the heated whole blood or plasma. A suitable isolation device is commercially available as the Clotalyst™ Autologous Thrombin Collection System (hereinafter "Clotalyst System"), sold by Biomet Biologics LLC, Warsaw, Ind., USA.

An exemplary device 100 for producing a clotting agent is shown in FIG. 1. A process for making the clotting agent begins with injecting a reagent comprising calcium chloride and ethanol into the main chamber 105 through the first port 110. Glass beads are also placed in the main chamber 105. After the reagent has been injected, the first port 110 is closed using the first replacement cap 115. Blood with anticoagulant is injected into the main chamber 105 through the second port 120. After the blood has been injected, the second port 120 is closed using the second replacement cap 125. Optionally, the syringes and blood separation device 400 are pre-heated to a temperature of about 25° C.

The contents of the device 100 are mixed by repeatedly inverting the device 100, e.g. about twelve times, so as to contact the blood with the glass beads. After mixing, the device is incubated The incubation process can be at a temperature and for a duration that will permit the contents of the device 100 to be heated at about 25° C. for about 15 minutes. Upon completion of the incubation period, a clotted mass of red blood cells, blood plasma, and glass beads forms at a second end 106 of the main chamber 105. After incubation is complete, the device 100 is shaken enough to dislodge and break-up any gel that may be present.

The clot extract may be otherwise contacted with a solid extraction material to produce a protein-containing liquid. This liquid is then isolated from the solid extraction material, as a Protein Solution of the present technology. Without limiting the scope, mechanism or function of the present technology, solid extraction materials useful herein concentrate cytokines or other proteins in the clot extract.

The solid extraction material can include various materials that provide a particular surface area to contact the cells. The solid extraction material may be a continuous material or may be discontinuous and comprise a plurality of separate particles. For example, the solid extraction material may be in the form of a plurality of beads, fibers, powder, a porous material, or a surface of a container comprising the clot extract. The solid extraction material may comprise geometric forms having various cross-sectional shapes, such as spherical, oval, or polygonal, among others. The solid extraction material can also comprise a continuous porous network, similar to a sponge, or can include a plurality of individual porous particles. The solid extraction material may also provide a larger surface area by being porous in comparison to a non-porous material.

In some embodiments, the solid extraction material includes particles having a large aspect ratio, for example, where the particles are needle-like in shape. The solid extraction material may also be formed as long fibers and may be or take a form similar to glass wool.

In some cases, the solid extraction material can comprise the internal walls of a container holding the liquid comprising white blood cells. For example, the solid extraction material may comprise the lumen of a syringe that contains the clot extract. Other containers include tubes, such as centrifuge tubes, or a blood fractionation device or concentrator assembly as described elsewhere herein.

Where the solid extraction material is a continuous material, such as a porous sponge-like material, the solid extraction material can be used in an amount sufficient to absorb or adsorb or include substantially the entire clot extract within the pores or interstices of the solid extraction material. Where the solid extraction material is a discontinuous material, such as a plurality of particles, the solid extraction material can be combined with the liquid containing the cells to form a slurry-like composition. The slurry can vary in consistency from paste-like, having a high-solids fraction, to a readily flowable slurry having a low-solids fraction.

The solid extraction material can provide a large surface area with which to contact clot extract. However, in some cases, the solid extraction material can be further treated to increase its surface area, for example, by physically or chemically etching or eroding the surface of the solid extraction material. With respect to chemical etching, a corrosive agent can be used to modify the surface of the solid extraction material depending on the nature of the material. The modified surface may be produced by employing an alkali or an acid, for example chromosulphonic acid, in particular about 20% to about 80% in strength, preferably about 50% chromosulphonic acid. The solid extraction material can be incubated with the corrosive agent for about 5 min to about 30 min in order to chemically etch the surface and increase the surface area. The solid extraction material can then be washed to remove the corrosive agent. For example, the solid extraction material can include the internal walls of a container for holding the clot extract where the internal walls are etched to subsequently increase the surface area in contact with the clot extract.

Various polymers, metals, ceramics, and glasses can be used as the solid extraction material. In some embodiments, the solid extraction material comprises a hygroscopic material. Examples of suitable solid extraction material materials include glasses, minerals, polymers, metals, and polysaccharides. Minerals include corundum and quartz. Polymers include polystyrene, polyethylene, polyvinyl chloride, polypropylene, and polyacrylamide. Metals include titanium. Polysaccharides include dextran and agarose. A preferred solid extraction material comprises, or consists essentially of, polyacrylamide, as further described below.

The solid extraction material may comprise, for example, continuous solid extraction material of glass or a plurality of glass particles, glass wool, a continuous solid extraction material of metal such as titanium, a plurality of metal beads, metal powder, and combinations thereof. A continuous solid extraction material of metal can include a block or other three-dimensional shape formed of porous metal or metal alloys with an open cell structure. The solid extraction material may include various beads or particles of various sizes including substantially spherical beads. Beads include polystyrene beads, polyacrylamide beads, glass beads, metal (e.g., titanium) beads, or any other appropriate beads. Beads may be any size appropriate for the container and the amount of liquid comprising white blood cells being used. In some instances, bead sizes can range from about 0.001 millimeters to about 3 millimeters in diameter. Where the bead size is sufficiently small, the beads can appear more like a powder.

Polyacrylamide beads used as the solid extraction material can be formed by polymerizing acrylamide monomer using controlled and standardized protocols as known in the art to produce relatively uniform beads formed of polyacrylamide gel. In general, polyacrylamide is formed by polymerizing acrylamide with a suitable bifunctional crosslinking agent, most commonly N,N'-methylenebisacrylamide (bisacrylamide). Gel polymerization is usually initiated with ammonium persulfate and the reaction rate is accelerated by the addition of a catalyst, such as N,N,N',N'-tetramethylethylenediamine (TEMED). In various embodiments, polyacrylamide beads comprise 0.5 micromole of carboxyl groups per milliliter of beads, imparting a slight anionic character (negative charge). The beads are also typically resistant to changes in pH, and are stable in many aqueous and organic solutions. By adjusting the total acrylamide concentration, the polyacrylamide gel can be formed in a wide range of pore sizes. Moreover, the polyacrylamide beads can be formed in many sizes and can have relatively uniform size distributions. Bead size may range from several micrometers in diameter to several millimeters in diameter. For example, various types of Bio-Gel™ P polyacrylamide gel beads (Bio-Rad Laboratories, Hercules, Calif., USA) have particle sizes ranging from less than about 45 μm up to about 180 μm. Polyacrylamide beads are also available from SNF Floerger (Riceboro, Ga., USA), Pierce Biotechnology, Inc. (Rockford, Ill., USA), and Polymers, Inc. (Fayetteville, Ark., USA).

Once polymerized, polyacrylamide beads can be dried and stored in a powder-like form. The dry beads are insoluble in water but can swell considerably upon being rehydrated. Rehydration returns the polyacrylamide beads to a gel consistency that can be from about two to about three times the dry state size. Thus, dry polyacrylamide beads (i.e., desiccating polyacrylamide beads) may be used to absorb a portion of a liquid volume, including solutes smaller than the bead pore size, and can serve to concentrate IL-1ra and other proteins produced by the white blood cells. For example, combining dry polyacrylamide beads with the blood and/or platelet-rich plasmaactivates production of IL-1ra by the white blood cells and also reduces the total liquid volume as the dry beads rehydrate and swell.

The solid extraction material is preferably sterilized, using techniques among known in the art, in order to prevent contamination of the clot extract. For example, heat and pressure sterilization methods, such as autoclaving, may be used depending on the particular composition of the solid extraction material. Alternative methods, such as chemical sterilization or irradiation, can be used where the solid extraction material may be adversely affected by the autoclaving process.

In some embodiments, the clot extract is incubated with solid extraction material for a time effective to remove a portion of the liquid. For example, the incubation may be 24 hours or less, 10 hours or less, 5 hours or less, 2 hours or less, 1 hour or less, 30 minutes or less, 15 minutes or less 10 minutes or less, 5 minutes or less, 4 minutes or less, 3, minutes or less, or 2 minutes or less. Incubation may be at least about 15 seconds, at least about 30 seconds, at least about 1 minutes, at least about 90 seconds, at least about 2 minutes, at least about 10 minutes, or at least about 30 minutes. In some embodiments, incubation s from about 1 minute to about 3 minutes. In some embodiments, the incubation is conducted at about 37° C. In some embodiments the liquid is not incubated, but is contacted with the solid extraction material for only so long as necessary to perform subsequent processing. The contacting may occur at ambient conditions, e.g., at a temperature of about 20-25° C.

In some embodiments, the clot extract and the solid extraction material are agitated to more thoroughly mix these components during contact. The agitation may be accomplished by inverting, shaking, rocking, stirring, or vortexing the liquid and solid extraction material. Agitation may increase contact of the clot extract with the solid extraction material. Agitation may be performed once, repeated multiple times, repeated periodically, or may be continuous. Additional aspects and features relating to producing protein-rich solutions using polyacrylamide beads and other solid extraction materials are described in: U.S. Patent Application Publication No. 2009/0220482, Higgins et al., published Sep. 3, 2009; U.S. Patent Application Publication No. 2010/0055087, Higgins et al., published Mar. 4, 2010; U.S. Patent Application Publication 2011/0052561, Hoeppner, published Mar. 3, 2011; International Application Publication 2012/030593, Higgins et al., published Mar. 8, 2012; and U.S. Patent Application Publication 2012/0172836, Higgins et al., published Jul. 5, 2012.

Contacting of clot extract with the solid extraction material may be performed using a suitable container or other apparatus to effect the contact. Contacting may be performed in a continuous process wherein a flow of the clot extract is passed over or through the solid extraction material, or the clot extract and solid extraction material may be contained in a vessel. As discussed above, the vessel may comprise the solid extraction material, or may merely serve as a container holding the beads or other forms of the material. Containers useful in the present technology include those known in the art, such as the Plasmax™ Plus Plasma Concentrator, commercially available from Biomet Biologics, LLC (Warsaw, Ind., USA) and may include those devices and methods of use as described in U.S. Pat. No. 7,553,413, Dorian et al., issued Jun. 30, 2009; and U.S. Pat. No. 7,694,828, Swift et al., issued Apr. 13, 2010.

Figure 2A:
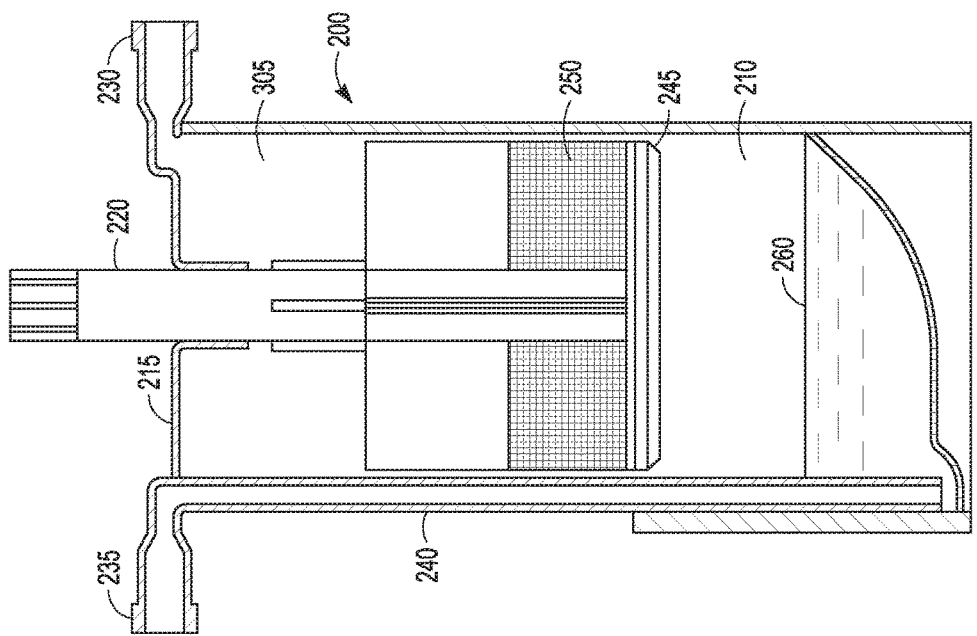
FIG. 2 shows a device for concentrating a blood clot extract to generate anti-inflammatory cytokines, before (FIG. 2A) and after (FIG. 2B) centrifugation.
Figure 2B:
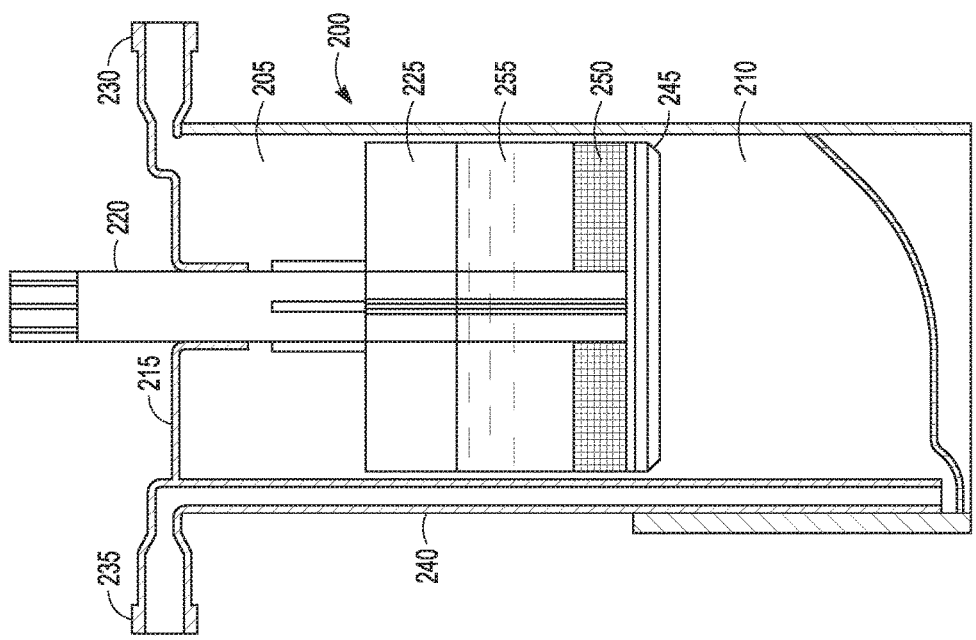

Such a device is shown in FIGS. 2A and 2B, for exemplary use with a polyacrylamide gel bead solid extraction material. The device 200 has an upper chamber 205 and a lower chamber 210. The upper chamber 205 has an end wall 215 through which the agitator stem 220 of a gel bead agitator 225 extends. The device 200 also has an inlet port 230 that extends through the end wall 215 and into the upper chamber 205. The device 200 also includes an outlet port 235 that communicates with a plasma concentrate conduit 240. The floor of upper chamber 205 includes a filter 245, the upper surface of which supports desiccated concentrating polyacrylamide beads 250.

During use, a fluid 255 containing the clot extract is injected to the upper chamber 205 via the inlet port 230 and mixed with the polyacrylamide beads 250. The fluid 255 and polyacrylamide beads 250 may be mixed by rotating the agitator stem 220 and the gel bead agitator 225, to help mix the fluid 255 and beads 250. The mixed fluid 255 and polyacrylamide beads 250 are then incubated for the desired time at the desired temperature. The device 200 is then centrifuged so that liquid passes to the lower chamber 210 while the polyacrylamide beads 250 are retained by a filter 245, thereby separating the polyacrylamide beads 250 from the resulting solution 260 of IL-1ra and other proteins that collects in the lower chamber 210. The solution 260 may be removed from the device via outlet port 235.

Obtaining Components from Tissue Cultures

Methods for making acellular Protein Solutions can comprise culturing cells in a cell culture that either naturally produce anti-inflammatory cytokines, such as IL-1ra, or cells that are engineered to produce such cytokines. Non-limiting examples of cells that naturally produce anti-inflammatory cytokines include adipose tissue cells, adipocytes, adipose-derived stem cells, stromal cells, bone marrow cells, mesenchymal stem cells, and blood cells.

In various embodiments, cell lines can be engineered to overproduce an anti-inflammatory cytokine. Non-limiting examples of anti-inflammatory cytokines include VEGF, TNF-α, IL-1ra, sTNF-RI, sTNF-RII, PGDF-AB, PDGF-BB, IGF-I, EGF, TGF-β1, sIL-1RII, and HGF. Stable eukaryotic cell lines can be generated that overexpress an anti-inflammatory cytokine by transfecting eukaryotic cells, such as mammalian cells, with recombinant DNA comprising a gene encoding an anti-inflammatory cytokine and a selectable marker. Alternatively, prokaryotes and yeast can be engineered to overexpress an anti-inflammatory cytokine by transformation with recombinant DNA comprising a gene encoding an anti-inflammatory cytokine and a selectable marker. Transformations and transfections can be performed with recombinant DNA molecules comprising a DNA sequencing encoding an anti-inflammatory cytokine, such as IL-1ra, and a selectable marker. Eukaryotic and prokaryotic cells can be engineered to overexpress the anti-inflammatory cytokine constitutively or by induction. Methods for expressing anti-inflammatory cytokines, such as IL-1ra, sTNF-RI, and sTNF-RII, and sIL1-RII in eukaryotic and prokaryotic cells are described in U.S. Pat. No. 6,337,072, Ford et al., issued Jan. 8, 2002; and U.S. Application Publication No. 2001/0053764, Sims et al., published Dec. 20, 2001.

When a IL-1ra gene is transcribed in humans, the mRNA can be spliced into four variants, resulting in four isoforms of translated IL-1ra. SEQ ID NOs: 1, 3, 5, and 7 are the cDNAs for IL-1ra isoforms 1-4 respectively, and SEQ ID NOs: 2, 4, 6, and 8 are the amino acid sequences of IL-1ra isoforms 1-4 respectively. Collectively, the IL-1ra isoforms are referred to as "IL-1ra." SEQ ID NO: 9 is the cDNA sequence for sTNF-RI and SEQ ID NO:10 is the amino acid sequence for sTNF-RI. SEQ ID NO:11 is the cDNA sequence for sTNF-RII and SEQ ID NO:12 is the amino acid sequence for sTNF-RII. SEQ ID NO:13 is the cDNA sequence for sIL-1RI and SEQ ID NO:14 is the amino acid sequence for sIL-1RI. SEQ ID NOs 15 and 17 are the cDNAs for sIL-1RIIv1 and sIL-1RIIv3 respectively, and SEQ ID NOs:16 and 18 are the amino acid sequences for sIL-1RIIv1 and sIL-1RIIv3 respectively. The cDNA sequence for IL-1RIIv2 is a non-coding sequence; therefore, it is not included.

To express either IL-1ra, sTNF-RI, or sTNF-RII (generically referred to as a "protein of interest") in a prokaryotic culture, for example in a particular bacteria, a cDNA sequence (SEQ ID NOs: 1, 3, 5, 7, 9, 11, 13, 15, or 17) is cloned into an expression vector suitable for the bacteria. The expression vector should comprise a strong promoter, and a selectable marker, such as antibiotic resistance. Non-limiting examples of antibiotics capable of killing bacteria cells include ampicillin, tetracycline, kanamycin, and chloramphenicol. The expression vector should further comprise elements that result in constitutive or inducible expression of the protein of interest. Optionally, a DNA sequence corresponding to a tag functionally coupled to the protein of interest that allows for identification and purification of the protein can be present in the vector adjacent to the gene for the protein of interest. For example, an N or C-terminal His tag can be used to detect proteins with anti-His antibodies, and they allow for purification on nickel columns. When the expression vector comprising a gene expressing a protein of interest is prepared, a bacteria cell, for example *E. coli*, can be transformed with the expression vector. The selectable marker ensures that only cells transformed with the vector will survive in LB broth supplemented with an antibiotic corresponding to the selectable marker. The bacteria can then be grown in LB broth supplemented with the antibiotic for expression and purification. Expression vectors, methods for cloning a protein of interest into an expression vector, methods for transforming prokaryotic cells, methods for expressing protein from transformed prokaryotic cells, and protein purification methods are commonly known by those with ordinary skill in the art.

To express a protein of interest in a eukaryotic culture, for example in mammalian cells, a cDNA sequence (SEQ ID NOs: 1, 3, 5, 7, 9, 11, 13, 15, or 17) is cloned into an expression vector suitable for a particular mammalian cell. The expression vector should comprise a strong promoter, and a selectable marker, such as antibiotic resistance. Non-limiting examples of antibiotics capable of killing mammalian cells include geneticin and gentamicin. The expression vector should further comprise elements that result in constitutive or inducible expression of the protein of interest. Optionally, a DNA sequence corresponding to a tag functionally coupled to the protein of interest that allows for identification and purification of the protein can be present in the vector adjacent to the gene for the protein of interest. When the expression vector comprising a gene expressing a protein of interest is prepared, a mammalian cell, such as a human cell, can be transfected with the expression vector. Transfected cells can be grown in a cell culture medium supplemented with an antibiotic corresponding to the selectable marker. The presence of the antibiotic allows for the isolation of stable cell lines. Stable cell lines can then be grown in cell culture medium supplemented with antibiotic for expression and purification. Expression vectors, methods for cloning a protein of interest into an expression vector, methods for transfecting eukaryotic cells and developing stable cell lines, methods for expressing protein from transfected eukaryotic cells, and protein purification methods are commonly known by those with ordinary skill in the art.

Alternatively, eukaryotic cells that have not been genetically altered by DNA transfection can be cultured. The eukaryotic cells can be primary cultures, i.e. cells grown directly from a eukaryotic donor, such as a human, or the eukaryotic cells can be established cell lines. Many established cell lines are available commercially from American Type Culture Collection, Inc. (Manassas, Va., USA). The cells can be grown with or an exogenous signal, such as a recombinant protein. Eukaryotic cells are often cultured in culture flasks with cell culture medium. The cell culture medium can be recovered from the flasks, and centrifuged to remove any non-adherent cells.

A cell culture can be a monolayer culture, a non-adherent culture, or a bioreactor. A monolayer culture comprises anchorage-dependent cells that are cultured on a suitable substrate that allows cell adhesion and spreading, such as cell culture flasks and cell culture dishes. A non-adherent culture comprises cells that are maintained in a suspension. Suitable cells are either not anchorage-dependent, or they are anchorage-dependent cells that have been adapted for culture in a suspension. Many cell lines, for example many insect cells, can be grown in either a monolayer or a suspension. A bioreactor is a device that can support a biologically active environment in which chemical processes are carried out and/or biochemically active substances are derived. Bioreactors can include suspended or immobilized cells. Monolayer cultures, non-adherent cultures, and bioreactors can be maintained by methods commonly used in the art.

In some embodiments, the cell culture is subjected to an electromagnetic field, so as to stimulate the production of one or more proteins. Stimulating the culture with an electromagnetic field may involve various forms of electromagnetic stimulation, such as a pulsed electromagnetic field or a capacitively coupled electromagnetic field. In some embodiments, the culture is stimulated using a power source coupled to a stimulation coil. The current passing through the coil produces a pulsing magnetic field which induces in the liquid a pulsing electric field. The coil may partially surround the culture as it is held within a container. The coil may be integrated into to the container holding the culture or may be removable. For example, a plastic tube can be formed with an integrated coil or the coil can be temporarily coupled to the container or placed within the container; for example, the tube can be configured so that the coil can be snapped onto the container. The power source can be coupled to the coil as needed to perform the stimulation.

Stimulation of the culture with an electromagnetic field may also include placing at least two electrodes across the liquid. Electrical energy may then be applied to the electrodes so as to capacitively couple the electrodes and generate the electromagnetic field there between. The electromagnetic field is therefore able to pass through the culture so as to increase the rate and/or amount of cytokine production. In other embodiments, electrodes can be used to produce a direct current or one or more coils can be used to produce a pulsed electromagnetic field.

The strength of the electromagnetic field during stimulation can be at least about 0.5 microvolts per centimeter, whether produced by direct current, capacitively coupled current, or pulsed electromagnetic field. In the case of a direct current electrode, the amplitude of the current can be from about 1 to about 200 microamperes, and in some embodiments, the amplitude may be from about 20 to about 100 microamperes. In still further embodiments, the current may be about 20, about 60, or about 100 microamperes. It should be understood, however, that the amplitude of the current may be of other suitable magnitudes.

The electromagnetic field applied during stimulation may be constant or vary over time. For example, a sinusoidal time varying electromagnetic field can be applied using the electrodes placed across the liquid. Such a sinusoidal time varying electromagnetic field can have a peak voltage across the electrodes from about 1 volt to about 10 volts, and in some embodiments, the peak voltage can be about 5 volts. The corresponding electric field produced can have an amplitude of from about 0.1 millivolt per centimeter (mV/cm) to about 100 mV/cm, and in some embodiments can be about 20 mV/cm. The sinusoidal time varying electric field may have a frequency of from about 1,000 Hz to about 200,000 Hz, and in some embodiments the frequency may be about 60,000 Hz.

The electromagnetic field applied to the culture may also be a pulsed electromagnetic field. The pulsed electromagnetic field can be induced using an external coil and a pulse generator. In this regard, a pulsed electromagnetic field may have a pulse duration of from about 10 microseconds per pulse to about 2000 microseconds per pulse. The pulse duration in one embodiment can be about 225 microseconds. The pulses may include electromagnetic bursts, in which a burst can comprise from 1 pulse to about 200 pulses. Alternatively, the electromagnetic field may have bursts that comprise from about 10 pulses to about 30 pulses. In this regard, in one embodiment each burst may comprise about 20 pulses.

The frequency at which bursts in the pulsed electromagnetic are applied may vary. In this regard, bursts can be repeated at a frequency of from about 1 Hz to about 100 Hz in some embodiments, and can be repeated at a frequency of about 10 Hz to about 20 Hz in other embodiments. Furthermore, bursts can repeat at a frequency of about 1.5 Hz, about 15 Hz or about 76 Hz. A burst can have a duration from about 10 microseconds up to about 40,000 microseconds. In this regard, a burst can have a duration of about 4.5 milliseconds.

Suitable devices for generating a capacitively coupled electromagnetic field include SpinalPak® spinal stimulator (EBI, L.P., Parsippany, N.J.) or a DC stimulation device such as an SpF® XL IIb spinal fusion stimulator (EBI, L.P., Parsippany, N.J.). Pulsed electromagnetic fields can be produced using various known methods and apparatuses, such as using a single coil or a pair of Helmholtz coils. For example, a suitable apparatus includes the EBI Bone Healing System® Model 2001 (EBI, L.P., Parsippany, N.J.) and the BTBS stimulation coil. With respect to direct current, an electric field may be generated using any known device for generating a direct current electric field, such as for example, the Osteogen™ implantable bone growth stimulator (EBI, L.P., Parsippany, N.J.). Other suitable devices for generating electromagnetic fields may be used.

Cell cultures can either release anti-inflammatory cytokines into culture medium naturally, or the cultures can be induced to release the anti-inflammatory cytokines into the culture medium. The culture medium can be isolated by aspiration, centrifugation or filtration for use in forming the acellular anti-inflammatory cytokine composition.

Obtaining Components from Urine

In some embodiments, an anti-inflammatory cytokine is isolated from urine, for use in producing a Protein Solution of the present technology. Proteins can be isolated from urine by methods among those known in the art. One such method is employed in the ProteoSpin™ Urine Protein Concentration Maxi Kit sold by Norgen Biotek Corp. (Thorold, Ontario, Canada). This kit utilizes an ion exchange resin integrated into a spin column. Briefly, a urine sample is obtained and its pH adjusted to 3.5. The urine is then transferred to a spin column containing the ion exchange resin, which is placed in a collection tube. The column is then centrifuged, wherein the proteins attach to the resin, and the remaining fluids and salts flow into the collection tube and are discarded. The proteins are then washed by applying supplied column activation and wash buffer followed by centrifugation. The flow through is discarded and the wash procedure is repeated. An elution buffer (10 mM sodium phosphate, pH 12.5) is added to the column and neutralizer is added to an elution tube. The spin column containing the elution buffer is placed in the elution tube and centrifuged, whereby the proteins are eluted and captured in the elution tube containing neutralizer.

Therapeutic Compositions

The present technology also provides compositions comprising a Protein Solution and a second component comprising active materials, physiological carriers, and combinations thereof. In some embodiments, compositions comprise a safe and effective amount of the Protein Solution and a safe and effective amount of a second active. A "safe and effective" amount of a component is an amount that is sufficient to have the desired therapeutic effect in the human or other mammalian subject, without undue adverse side effects (such as toxicity, irritation, or allergic response), commensurate with a reasonable benefit/risk ratio when used in the manner of this technology. The specific safe and effective amount of the component will, obviously, vary with such factors as the particular condition being treated, the physical condition of the patient, the nature of concurrent therapy (if any), the specific components used, the specific route of administration and dosage form, the carrier (if any) employed, and the desired dosage regimen.

Active materials among those useful herein include biologics and pharmaceutical actives. Biologics include blood fractions, such as PRP, blood products, and concentrated bone marrow aspirate (cBMA). Accordingly, in some embodiments, the present technology provides compositions comprising a safe and effective amount of a Protein Solution and a safe and effective amount of cBMA. An autologous therapeutic composition comprises APS and cBMA in an APS:cBMA ratio of about 1:1, about 1:2, about 1:3, about 1:4, about 1:5, about 1:6, about 1:7, about 1:8, about 1:9 or about 1:10. Alternatively, the APS:cBMA ratio can be about 2:1, about 3:1, about 4:1, about 5:1, about 6:1, about 7:1, about 8:1, about 9:1 or about 10:1. cBMA can include hematopoietic, stem cells, stromal stem cells, mesenchymal stem cells, endothelial progenitor cells, red blood cells, white blood cells, fibroblasts, reticulocytes, adipose cells, or endothelial cells. Methods for producing cBMA among those useful herein are described in U.S. Application Publication No. 2006/0278588, Woodell-May, published Dec. 14, 2006.

Pharmaceutical actives among those useful herein include herein include organic molecules, proteins, peptides, peptidomimetics, nucleic acids, nucleoproteins, antisense molecules, polysaccharides, glycoproteins, lipoproteins, carbohydrates and polysaccharides, botanical extracts, and synthetic and biologically engineered analogs thereof, living cells (other than white blood cells stromal cells) such as chondrocytes, bone marrow cells, viruses and virus particles, natural extracts, and combinations thereof. Specific non-limiting examples of bioactive materials include hormones, antibiotics and other anti-infective agents, hematopoietics, thrombopoietics, antiviral agents, antitumor agents (chemotherapeutic agents), antipyretics, analgesics, anti-inflammatory agents, antiallergy agents, vasodilators, cytokines, growth factors, gene regulators, vitamins, minerals and other nutritionals, nutraceuticals and combinations thereof. In particular, actives include bronchodilators (such as albuterol, levabuterol, irbuterol, ipatropium, salmeterol, and formoterol), glucocorticosteroids (such as mometasone, fluticasone, budesonide, and beclomethosone), antibiotics, antivirals, and combinations thereof. In some embodiments, compositions may comprise growth factors in addition to those present in the Protein Solution, such Platelet-Derived Growth Factor (PDGF), Transforming Growth Factor Beta (TGF-$\beta$), Insulin-Like Growth Factor (IGF), Fibroblast Growth Factor (FGF), Epidermal Growth Factor (EGF), Vascular Endothelial Growth Factor (VEGF), and Bone Morphogenetic Proteins (BMPs).

In some embodiments, Protein Solutions comprise one or more cytokines derived from a tissue comprising white blood cells, by contacting a liquid comprising white blood cells with a solid extraction material. Liquids comprising white blood cells include blood, adipose tissue, bone marrow, and fractions thereof, such as platelet-rich plasma. Solid extraction materials include those described above. Devices for making blood fractions by centrifugation of whole blood are described in U.S. Pat. No. 7,992,725, Leach et al., issued Aug. 9, 2011, U.S. Pat. No. 7,374,678, Leach, issued May 20, 2008; U.S. Pat. No. 7,179,391 to Leach et al., issued Feb. 20, 2007; U.S. Pat. No. 7,992,725, Leach et al., issued Aug. 9, 2011; U.S. Pat. No. 7,806,276, Leach et al., issued Oct. 5, 2010; and U.S. Pat. No. 8,048,297, Leach et al., issued Nov. 1, 2011. Methods for making solutions rich in cytokines are described in U.S. Patent Application Publication No. 2009/0220482, Higgins et al., published Sep. 3, 2009; U.S. Patent Application Publication No. 2010/0055087, Higgins et al., published Mar. 4, 2010; U.S. Patent Application Publication 2011/0052561, Hoeppner, published Mar. 3, 2011; International Application Publication 2012/030593, Higgins et al., published Mar. 8, 2012; and U.S. Patent Application Publication 2012/0172836, Higgins et al., published Jul. 5, 2012. Compositions and methods useful in aspects of the present technology are also described in the following applications filed concurrently with this disclosure: U.S. patent application Ser. No. 13/840,562, Binder et al., filed on Mar. 15, 2013, Methods and Non-immunogenic Compositions for Treating Inflammatory Diseases; U.S. patent application Ser. No. 13/841,083, Landrigan, et al., filed on Mar. 15, 2013, Treatment of Inflammatory Respiratory Disease Using Protein Solutions; U.S. patent application Ser. No. 13/837,480, O'Shaughnessey, et al., filed on Mar. 15, 2013, Treatment of Pain Using Protein Solutions; U.S. patent application Ser. No. 13/839,280, Leach et al., filed on Mar. 15, 2013, Methods for Making Cytokine Compositions from Tissue Using Non-Gravimetric Methods; U.S. patent application Ser. No. 13/840,129, Matusuka, et al., filed on Mar. 15, 2015 Treatment of Collagen Defects Using Protein Solutions; and U.S. patent application Ser. No. 13/841,103, Landrigan, et al., filed on Mar. 15, 2013, Treatment of Peripheral Vascular Disease Using Protein Solutions, all of which are incorporated by reference herein.

The compositions may comprise a carrier material, in addition to any liquid comprising the Protein Solution. It should be understood that in various embodiments of the present technology, methods of treatment employ the Protein Solution as comprised and made above, without further carrier, by direct injection or other application to the site of treatment. However, in other embodiments, an additional carrier material may be used for such reasons as for ease of administration, to facilitate administration using a particular delivery device, enhancing activity, an increasing the length of time the Protein Solution remains at the site of administration. Carriers among those useful herein include saline, hyaluronic acid, collagen, buffers (such as Hank's Buffer), cell culture media, blood products (such as PRP and platelet poor plasma), bone marrow aspirate, concentrated bone marrow aspirate, and mixtures thereof.

Protein Solutions, and compositions comprising Protein Solutions may be sterilized prior to administration, by any suitable method. For example, a Protein Solution may be sterilized by including a sterile filter to process the product made by the processes described above. In some embodiments, an antibiotic may be included in the solid extraction material during the contacting step described above, or may be added at one or more of the various steps in the methods and treatments described herein. Alternatively, or in addition, the Protein Solution may be produced aseptically.

Protein Solutions and compositions comprising Protein Solutions may also be lyophilized (freeze drying, or cryodesiccation) after production, using methods among those known in the art. When freeze dried, the anti-inflammatory cytokine composition can be hydrated at a time before administration or at a time of administration. Hydration may be accomplished by mixing the composition with a solution including saline, buffers, blood, blood fractions, bone marrow aspirate, concentrated bone marrow aspirate, and combinations thereof.

The present technology provides compositions comprising components derived from blood or other tissue that are suitable for allogeneic administration. In particular, such compositions may comprise proteins and other components isolated from a mammalian subject, or a plurality of mammalian subjects, other than the subject to whom the composition is to be administered in a method of this technology. In some embodiments, Protein Solutions comprise components isolated from the subject to be treated and components isolated from one or more subjects other than the subject to be treated.

Methods of Treatment

The present technology provides methods for the treatment of an inflammatory disorder or other disorder mediated by IL1-ra in a human or other mammalian subject, comprising administration of a Protein Solution of the present technology to the subject. Such diseases may be characterized by elevated neutrophil counts. Without limiting the mechanism, utility or function of the present technology, the methods and treatments of this technology mediate the effects of interleukin-1 and its role in the inflammation cascade. As generally discussed above, interleukin-1 (IL-1) includes a family of cytokines that can stimulate lymphocytes, neutrophils, and macrophages, activate phagocytes, increase airway fibrosis, promote lymphocyte nodules in the airways, increase production of both MMP-9 and MMP-12, and are involved in many chronic inflammatory conditions. IL-1 can be generated by macrophages, monocytes, and dendritic cells, and can be part of the inflammatory response against infection. See, Lappalainen et al., "Interleukin-1β Causes Pulmonary Inflammation, Emphysema, and Airway Remodeling in the Adult Murine Lung" American Journal of Respiratory Cell and Molecular Biology, vol. 32, no. 4, pages 311-318 (April 2005).

The mode of action of IL-1 can be mediated by IL-1ra. IL-1ra binds to the same receptor on the cell surface as IL-1, and thus prevents IL-1 from sending a signal to that cell. IL-1ra is secreted from white blood cells, including monocytes, macrophages, neutrophils, polymorphonuclear cells (PMNs), and other cells, and can modulate a variety of IL-1 related immune and inflammatory responses, as described by Arend W P, Malyak M, Guthridge C J, Gabay C (1998) "Interleukin-1 receptor antagonist: role in biology" Annu. Rev. Immunol. 16: 27-55. Production of IL-1ra is stimulated by several substances including adherent immunoglobulin G (IgG), other cytokines, and bacterial or viral components. Likewise, the mode of action of TNF-α can be mediated by sTNF-RI and sTNF-RII, which prevent TNF-α from binding to membrane bound TNF-RI and/or TNF-RII.

Examples of inflammatory disorders treated by the methods of this technology include rheumatoid arthritis, osteoarthritis, osteolytis, tendonitis, synovitis, peripheral vascular disease, and inflammatory respiratory diseases (such as chronic obstructive pulmonary disease, fibrosis, emphysema, acute respiratory distress syndrome, and pneumonia). Treatment methods also include the prevention, reduction or elimination of pain associated with various disorders, such as pain associated with traumatic injury, muscle strain, arthritis (rheumatoid arthritis and osteoarthritis), synovitis, sacroiliac joint disorders, back disorders, post-surgical injections, tendon injections, sports medicine procedure (for example, ACL repair, MCL repair, BTB repair, patella repair, or cartilage repair), contusions, muscle strains, post traumatic osteoarthritis. Methods also include stimulation of chondrocyte production at the site of a collagen defect, such as defects at joints associated with arthritis, injuries or surgical procedures.

In some embodiments, methods of the present technology comprise administration of a Protein Solution to the site of a tissue defect to prevent or treat a disorder associated with IL-1ra. As referred to herein, such "tissue defects" include any condition involving tissue which is inadequate for physiological or cosmetic purposes. Examples of such defects include those that are congenital, those that result from or are symptomatic of disease, disorder, or trauma, and those that are consequent to surgical or other medical procedures. Embodiments include treatment for vascular, bone, skin, nerve, and organ tissue defects. Examples of such defects include those resulting from osteoporosis, spinal fixation procedures, hip and other joint replacement procedures, chronic wounds, fractures, sclerosis of tissues and muscles, and spinal cord or other nerve injury. In various embodiments, the compositions and methods of this invention may be used in methods associated with the repair bone or cartilage defects.

In various embodiments, methods are for the treatment of inflammatory disorders in a human. In other embodiments, treatment is for non-human mammals, such as companion, working, and sports animals. For example, such methods of this technology may be used for the treatment of inflammatory disorders in horses.

In various embodiments, methods of the present technology comprise a point-of-care method for making a Protein Solution. As referred to herein, a "point-of-care method" wherein the processes of the present technology, e.g., production of a Protein Solution from blood clots or urine, are performed at a time proximate to the administration of the Protein Solution to the subject being treated. Such methods may be performed at a location proximate, such as in the same room (for example, bed side) or otherwise immediately adjacent, to the mammalian subject to be transfused with the RBCs. In various embodiments, a "proximate time" may be, for example, within 12 hours, within 8 hours, within 2 hours, within 1 hour or within 30 minutes of administration of the Protein Solution to the subject.

In some embodiments, the Protein Solution is administered with a concomitant therapy. Such therapies include, for example, the administration of pharmaceutical actives or biologics, as described above. In some embodiments, concomitant therapies are administered concurrently with a Protein Solution. For example, methods may comprise administration of a Protein Solution with a safe and effective amount of an active selected from the group consisting of glucocorticosteroids, non-steroidal anti-inflammatories, antibiotics, antivirals, and combinations thereof.

In some embodiments, methods comprise administration of a Protein Solution with concentrated bone marrow aspirate, as described above. For example, cBMA and a Protein Solution may be administered concomitantly.

Methods of the present technology generally comprise administration of a Protein Solution to the site of inflammation in a mammalian subject. Administration of the Protein Solution can be performed with any suitable device, including such devices known in the art for topical delivery of compositions to the muscle, joint, vascular, lung or other tissue. For example, topical delivery for treatment of inflammation or pain associated with joint disorders may comprise injection of a Protein Solution at or near the joint. Treatment for inflammatory respiratory diseases may comprise delivery of a Protein Solution by endotracheal tubes, inhalers and nebulizers.

Non-Limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The disclosure of all patents and patent applications cited in this disclosure are incorporated by reference herein.

The description and specific examples, while indicating embodiments of the technology, are intended for purposes of illustration only and are not intended to limit the scope of the technology. Equivalent changes, modifications and variations of specific embodiments, materials, compositions and methods may be made within the scope of the present technology, with substantially similar results. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "prefer" or "preferable" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein. Further, as used herein the term "consisting essentially of" recited materials or components envisions embodiments "consisting of" the recited materials or components.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters.

As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

What is claimed is:

1. A substantially acellular anti-inflammatory cytokine composition comprising:
   interleukin-1 receptor antagonist (IL-1ra);
   soluble tumor necrosis factor receptor I (sTNF-RI);
   soluble tumor necrosis factor receptor II (sTNF-RII); and
   at least one growth factor selected from epidermal growth factor (EGF), hepatocyte growth factor (HGF), and platelet-derived growth factor BB (PDGF-BB);
   wherein at least one of the IL-1ra, sTNF-RI, sTNF-RII and the selected growth factor is isolated from urine, clotted blood, or tissue culture, the at least one growth factor having a concentration greater than the concentration of the at least one growth factor in normal blood, and wherein the composition is substantially free of viable cells.

2. The anti-inflammatory composition according to claim 1, wherein the IL1ra has a concentration of at least about 10,000 pg/ml, and the sTNF-RI has a concentration of at least about 1,200 pg/ml.

3. The anti-inflammatory composition according to claim 1, wherein the selected growth factor is epidermal growth factor and has a concentration of at least about 800 pg/ml.

4. The anti-inflammatory composition according to claim 1, further comprising soluble interleukin-1 receptor II (sIL-1RII).

5. The anti-inflammatory composition according to claim 1, wherein the growth factor has a concentration of at least about 3000 pg/ml.

6. The anti-inflammatory composition according to claim 1, wherein the anti-inflammatory cytokine composition is freeze dried such that the composition is substantially free of viable cells.

7. The anti-inflammatory composition according to claim 1, wherein the interleukin-1 receptor antagonist is derived from urine.

8. The anti-inflammatory composition according to claim 1, wherein the interleukin-1 receptor antagonist is derived from tissue culture.

9. The anti-inflammatory composition according to claim 1, wherein the interleukin-1 antagonist is derived from a blood clot.

10. The anti-inflammatory composition according to claim 1, further comprising a carrier material selected from hyaluronic acid, collagen or a mixture thereof.

11. A substantially acellular composition for the treatment of a disorder mediated by interleukin-1 (IL-1) comprising:
   at least about 25,000 pg/ml interleukin-1 receptor antagonist (IL-1ra);
   at least about 2,500 pg/ml soluble tumor necrosis factor receptor II (sTNF-RII); and
   a protein selected from epidermal growth factor, hepatocyte growth factor, and platelet-derived growth factor BB, wherein the concentration of the selected protein in the composition is greater than the concentration of the selected protein in normal blood;
   wherein the composition is substantially acellular.

12. The composition according to claim 11, wherein at least one of IL-1ra, sTNF-RII, and the selected protein is isolated from urine, clotted blood, or tissue culture.

13. The composition according to claim 11, wherein at least one of IL-1ra, sTNF-RII, and the selected protein is obtained from culture medium from a monolayer cell culture, a bioreactor, or a non-adherent cell culture.

14. The composition according to claim 11, further comprising soluble interleukin-1 receptor II (sIL-1RII).

15. The composition according to claim 11, wherein the composition is freeze dried such that the composition is substantially free of viable cells.

16. The composition according to claim 11, wherein the selected protein is epidermal growth factor and has a concentration of at least about 800 pg/ml.

17. The composition according to claim 11, further comprising hyaluronic acid, collagen, or a mixture thereof.

18. A anti-inflammatory composition comprising:
   soluble tumor necrosis factor receptor II (sTNF-RII); and
   at least one growth factor selected from epidermal growth factor (EGF), hepatocyte growth factor (HGF), and platelet-derived growth factor BB (PDGF-BB), the at least one growth factor have a concentration greater than the concentration of the at least one growth factor in normal blood;
   wherein at least one of the sTNF-RII and the selected growth factor is isolated from urine, clotted blood, or tissue culture and the composition is substantially free of viable cells.

19. The composition of claim 18, wherein the sTNF-RII has a concentration of at least about 2,500 pg/ml.

20. The composition according to claim 18, wherein the sTNF-RII has a concentration of at least three times the concentration of sTNF-RII in normal blood.

21. The composition of claim 18, wherein the selected growth factor is epidermal growth factor and has a concentration of at least about 800 pg/ml.

22. The composition of claim 18, wherein the selected growth factor has a concentration at least about twice the concentration of the selected growth factor in normal blood.

23. The composition according to claim 18, further comprising interleukin-1 receptor antagonist at a concentration of at least about 10,000 pg/ml.

24. The composition according to claim 18, further comprising soluble tumor necrosis factor receptor I (sTNF-RI) at a concentration of at least about 1,200 pg/ml.

25. The composition according to claim 18, further comprising soluble interleukin-1 receptor II (sIL-1RII).

26. The composition according to claim 25, wherein the sIL-1RII has a concentration at least about twice the concentration of sIL-1RII in normal blood.

27. The composition according to claim 18, further comprising a carrier material selected from hyaluronic acid, collagen or a mixture thereof.

28. The composition according to claim 18, wherein the composition is freeze dried such that the composition is substantially free of viable cells.

\* \* \* \* \*

UNITED STATES PATENT AND TRADEMARK OFFICE
CERTIFICATE OF CORRECTION

PATENT NO. : 9,758,806 B2  
APPLICATION NO. : 13/837005  
DATED : September 12, 2017  
INVENTOR(S) : Woodell-May et al.

Page 1 of 2

It is certified that error appears in the above-identified patent and that said Letters Patent is hereby corrected as shown below:

On the Title Page

In Column 2, under "Other Publications", Line 4, delete "IL-1b and TNFa-stimulated" and insert --IL-1β and TNFα-stimulated-- therefor In Column 2, under "Other Publications", Line 14, delete "homrone" and insert --hormone-- therefor In item (57), in "Abstract", in Column 2, Line 2, delete "sTNF-R1," and insert --sTNF-RI,-- therefor On page 3, in Column 1, under "Other Publications", Line 3-4, delete "factor-alpha" and insert --factor-α-- therefor On page 3, in Column 1, under "Other Publications", Line 30, delete "acive" and insert --active-- therefor On page 4, in Column 1, under "Other Publications", Line 2, delete "IL-1beta" and insert --IL-1β-- therefor On page 4, in Column 1, under "Other Publications", Line 15, delete ""Therapuetic" and insert --"Therapeutic-- therefor On page 4, in Column 1, under "Other Publications", Line 19, delete ""Intratrachael" and insert --"Intratracheal-- therefor On page 5, in Column 1, under "Other Publications", Line 56, delete "railed" and insert --mailed-- therefor On page 5, in Column 2, under "Other Publications", Line 17, delete "pgs pgs." and insert --pgs.-- therefor Signed and Sealed this  
Ninth Day of April, 2019

Andrei Iancu  
*Director of the United States Patent and Trademark Office*

CERTIFICATE OF CORRECTION (continued)
U.S. Pat. No. 9,758,806 B2

On page 5, in Column 2, under "Other Publications", Line 67, delete "o" and insert --to-- therefor On page 6, in Column 2, under "Other Publications", Line 27, delete "ensor" and insert --tensor-- therefor On page 6, in Column 2, under "Other Publications", Line 51, delete "preclincial" and insert --preclinical-- therefor On page 7, in Column 2, under "Other Publications", Line 1, delete ""international" and insert --"International-- therefor On page 7, in Column 2, under "Other Publications", Line 27, delete "Ovariectornized" and insert --Ovariectomized-- therefor In the Claims In Column 45, Line 40, in Claim 2, delete "IL1ra" and insert --IL-1ra-- therefor

SEQUENCE LISTING

```
<160> NUMBER OF SEQ ID NOS: 18

<210> SEQ ID NO 1
<211> LENGTH: 534
<212> TYPE: DNA
<213> ORGANISM: Homo sapiens

<400> SEQUENCE: 1
```

```
atggaaatct gcagaggcct ccgcagtcac ctaatcactc tcctcctctt cctgttccat    60
tcagagacga tctgccgacc ctctgggaga aatccagca agatgcaagc cttcagaatc   120
tgggatgtta accagaagac cttctatctg aggaacaacc aactagttgc tggatacttg   180
caaggaccaa atgtcaattt agaagaaaag atagatgtgg tacccattga gcctcatgct   240
ctgttcttgg gaatccatgg agggaagatg tgcctgtcct gtgtcaagtc tggtgatgag   300
accagactcc agctggaggc agttaacatc actgacctga gcgagaacag aaagcaggac   360
aagcgcttcg ccttcatccg ctcagacagt ggccccacca ccagttttga gtctgccgcc   420
tgccccggtt ggttcctctg cacagcgatg aagctgacc agcccgtcag cctcaccaat   480
atgcctgacg aaggcgtcat ggtcaccaaa ttctacttcc aggaggacga gtag         534
```

<210> SEQ ID NO 2
<211> LENGTH: 177
<212> TYPE: PRT
<213> ORGANISM: Homo sapiens

<400> SEQUENCE: 2

```
Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
                20                  25                  30

Ser Lys Met Gln Ala Phe Arg Ile Trp Asp Val Asn Gln Lys Thr Phe
            35                  40                  45

Tyr Leu Arg Asn Asn Gln Leu Val Ala Gly Tyr Leu Gln Gly Pro Asn
        50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
                100                 105                 110

Leu Ser Glu Asn Arg Lys Gln Asp Lys Arg Phe Ala Phe Ile Arg Ser
            115                 120                 125

Asp Ser Gly Pro Thr Thr Ser Phe Glu Ser Ala Ala Cys Pro Gly Trp
        130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```

<210> SEQ ID NO 3
<211> LENGTH: 543
<212> TYPE: DNA
<213> ORGANISM: Homo sapiens

<400> SEQUENCE: 3

```
atggctttag ctgacttgta tgaagaagga ggtggaggag gaggagaagg tgaagacaat    60
gctgactcaa aggagacgat ctgccgaccc tctggagaa aatccagcaa gatgcaagcc   120
ttcagaatct gggatgttaa ccagaagacc ttctatctga ggaacaacca actagttgct   180
ggatacttgc aaggaccaaa tgtcaattta gaagaaaaga tagatgtggt acccattgag   240
cctcatgctc tgttcttggg aatccatgga gggaagatgt gcctgtcctg tgtcaagtct   300
```

```
ggtgatgaga ccagactcca gctggaggca gttaacatca ctgacctgag cgagaacaga    360
aagcaggaca agcgcttcgc cttcatccgc tcagacagtg gccccaccac cagttttgag    420
tctgccgcct gccccggttg gttcctctgc acagcgatgg aagctgacca gcccgtcagc    480
ctcaccaata tgcctgacga aggcgtcatg gtcaccaaat ctacttccag gaggacgag     540 tag                                                                  543
```

```
<210> SEQ ID NO 4
<211> LENGTH: 180
<212> TYPE: PRT
<213> ORGANISM: Homo sapiens

<400> SEQUENCE: 4
```

```
Met Ala Leu Ala Asp Leu Tyr Glu Glu Gly Gly Gly Gly Gly Glu
  1               5                  10                  15

Gly Glu Asp Asn Ala Asp Ser Lys Glu Thr Ile Cys Arg Pro Ser Gly
             20                  25                  30

Arg Lys Ser Ser Lys Met Gln Ala Phe Arg Ile Trp Asp Val Asn Gln
         35                  40                  45

Lys Thr Phe Tyr Leu Arg Asn Asn Gln Leu Val Ala Gly Tyr Leu Gln
     50                  55                  60

Gly Pro Asn Val Asn Leu Glu Glu Lys Ile Asp Val Val Pro Ile Glu
 65                  70                  75                  80

Pro His Ala Leu Phe Leu Gly Ile His Gly Gly Lys Met Cys Leu Ser
                 85                  90                  95

Cys Val Lys Ser Gly Asp Glu Thr Arg Leu Gln Leu Glu Ala Val Asn
            100                 105                 110

Ile Thr Asp Leu Ser Glu Asn Arg Lys Gln Asp Lys Arg Phe Ala Phe
        115                 120                 125

Ile Arg Ser Asp Ser Gly Pro Thr Thr Ser Phe Glu Ser Ala Ala Cys
    130                 135                 140

Pro Gly Trp Phe Leu Cys Thr Ala Met Glu Ala Asp Gln Pro Val Ser
145                 150                 155                 160

Leu Thr Asn Met Pro Asp Glu Gly Val Met Val Thr Lys Phe Tyr Phe
                165                 170                 175

Gln Glu Asp Glu
            180
```

```
<210> SEQ ID NO 5
<211> LENGTH: 480
<212> TYPE: DNA
<213> ORGANISM: Homo sapiens

<400> SEQUENCE: 5
atggctttag agacgatctg ccgaccctct gggagaaaat ccagcaagat gcaagccttc     60
agaatctggg atgttaacca agaagccttc tatctgagga caaccaact agttgctgga    120 tacttgcaag gaccaaatgt caatttagaa gaaagatag atgtggtacc cattgagcct    180
catgctctgt tcttgggaat ccatggaggg aagatgtgcc tgtcctgtgt caagtctggt    240
gatgagacca gactccagct ggaggcagtt aacatcactg acctgagcga gaacagaaag    300
caggacaagc gcttcgcctt catccgctca gacagtggcc ccaccaccag ttttgagtct    360
gccgcctgcc ccggttggtt cctctgcaca gcgatggaag ctgaccagcc cgtcagcctc    420
accaatatgc ctgacgaagg cgtcatggtc accaaattct acttccagga ggacgagtag    480
```

<210> SEQ ID NO 6
<211> LENGTH: 159
<212> TYPE: PRT
<213> ORGANISM: Homo sapiens

<400> SEQUENCE: 6

Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
                85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
        115                 120                 125

Cys Thr Ala Met Glu Ala Asp Gln Pro Val Ser Leu Thr Asn Met Pro
    130                 135                 140

Asp Glu Gly Val Met Val Thr Lys Phe Tyr Phe Gln Glu Asp Glu
145                 150                 155

<210> SEQ ID NO 7
<211> LENGTH: 432
<212> TYPE: DNA
<213> ORGANISM: Homo sapiens

<400> SEQUENCE: 7
atgcaagcct tcagaatctg ggatgttaac cagaagacct tctatctgag gaacaaccaa      60
ctagttgctg gatacttgca aggaccaaat gtcaatttag aagaaagat agatgtggta     120 cccattgagc ctcatgctct gttcttggga atccatggag ggaagatgtg cctgtcctgt     180
gtcaagtctg gtgatgagac cagactccag ctggaggcag ttaacatcac tgacctgagc     240
gagaacagaa agcaggacaa gcgcttcgcc ttcatccgct cagacagtgg ccccaccacc     300
agttttgagt ctgccgcctg ccccggttgg ttcctctgca cagcgatgga agctgaccag     360
cccgtcagcc tcaccaatat gcctgacgaa ggcgtcatgg tcaccaaatt ctacttccag     420
gaggacgagt ag                                                         432

<210> SEQ ID NO 8
<211> LENGTH: 143
<212> TYPE: PRT
<213> ORGANISM: Homo sapiens

<400> SEQUENCE: 8

Met Gln Ala Phe Arg Ile Trp Asp Val Asn Gln Lys Thr Phe Tyr Leu
1               5                   10                  15

Arg Asn Asn Gln Leu Val Ala Gly Tyr Leu Gln Gly Pro Asn Val Asn
            20                  25                  30

Leu Glu Glu Lys Ile Asp Val Val Pro Ile Glu Pro His Ala Leu Phe
        35                  40                  45

Leu Gly Ile His Gly Gly Lys Met Cys Leu Ser Cys Val Lys Ser Gly
 50                  55                  60

Asp Glu Thr Arg Leu Gln Leu Glu Ala Val Asn Ile Thr Asp Leu Ser
 65                  70                  75                  80

Glu Asn Arg Lys Gln Asp Lys Arg Phe Ala Phe Ile Arg Ser Asp Ser
                 85                  90                  95

Gly Pro Thr Thr Ser Phe Glu Ser Ala Ala Cys Pro Gly Trp Phe Leu
            100                 105                 110

Cys Thr Ala Met Glu Ala Asp Gln Pro Val Ser Leu Thr Asn Met Pro
            115                 120                 125

Asp Glu Gly Val Met Val Thr Lys Phe Tyr Phe Gln Glu Asp Glu
            130                 135                 140

<210> SEQ ID NO 9
<211> LENGTH: 1368
<212> TYPE: DNA
<213> ORGANISM: Homo sapiens

<400> SEQUENCE: 9

| | | | | | |
|---|---|---|---|---|---|
| atgggcctct | ccaccgtgcc | tgacctgctg | ctgccactgg | tgctcctgga | gctgttggtg | 60 |
| ggaatatacc | cctcagggt | tattggactg | tccctcacc | taggggacag | ggagaagaga | 120 |
| gatagtgtgt | gtccccaagg | aaaatatatc | caccctcaaa | ataattcgat | tgctgtacc | 180 |
| aagtgccaca | aaggaaccta | cttgtacaat | gactgtccag | gccgggggca | ggatacggac | 240 |
| tgcagggagt | gtgagagcgg | ctccttcacc | gcttcagaaa | accacctcag | acactgcctc | 300 |
| agctgctcca | atgccgaaa | ggaaatgggt | caggtggaga | tctcttcttg | cacagtggac | 360 |
| cgggacaccg | tgtgtggctg | caggaagaac | cagtaccggc | attattggag | tgaaaacctt | 420 |
| ttccagtgct | tcaattgcag | cctctgcctc | aatgggaccg | tgcacctctc | ctgccaggag | 480 |
| aaacagaaca | ccgtgtgcac | ctgccatgca | ggtttctttc | taagagaaaa | cgagtgtgtc | 540 |
| tcctgtagta | actgtaagaa | aagcctggag | tgcacgaagt | tgtgcctacc | ccagattgag | 600 |
| aatgttaagg | gcactgagga | ctcaggcacc | acagtgctgt | tgcccctggt | cattttcttt | 660 |
| ggtctttgcc | ttttatccct | cctcttcatt | ggtttaatgt | atcgctacca | acggtggaag | 720 |
| tccaagctct | actccattgt | ttgtgggaaa | tcgacacctg | aaaaagaggg | ggagcttgaa | 780 |
| ggaactacta | ctaagcccct | ggccccaaac | ccaagcttca | gtcccactcc | aggcttcacc | 840 |
| cccacccctgg | gcttcagtcc | cgtgcccagt | tccaccttca | cctccagctc | cacctatacc | 900 |
| cccggtgact | gtcccaactt | tgcggctccc | cgcagagagg | tggcaccacc | ctatcagggg | 960 |
| gctgacccca | tccttgcgac | agccctcgcc | tccgacccca | tccccaaccc | ccttcagaag | 1020 |
| tgggaggaca | cgcgccacaa | gccacagagc | ctagacactg | atgaccccgc | gacgctgtac | 1080 |
| gccgtggtgg | agaacgtgcc | cccgttgcgc | tggaaggaat | tcgtgcggcg | cctagggctg | 1140 |
| agcgaccacg | agatcgatcg | gctggagctg | cagaacgggc | gctgcctgcg | cgaggcgcaa | 1200 |
| tacagcatgc | tggcgacctg | gaggcggcgc | acgccgcggc | gcgaggccac | gctggagctg | 1260 |
| ctgggacgcg | tgctccgcga | catggaccctg | ctgggctgcc | tggaggacat | cgaggaggcg | 1320 |
| ctttgcggcc | ccgccgccct | cccgcccgcg | cccagtcttc | tcagatga | | 1368 |

<210> SEQ ID NO 10
<211> LENGTH: 455
<212> TYPE: PRT
<213> ORGANISM: Homo sapiens

<400> SEQUENCE: 10

```
Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415
```

Thr Leu Glu Leu Leu Gly Arg Val Leu Arg Asp Met Asp Leu Leu Gly
                420                 425                 430

Cys Leu Glu Asp Ile Glu Glu Ala Leu Cys Gly Pro Ala Ala Leu Pro
            435                 440                 445

Pro Ala Pro Ser Leu Leu Arg
    450                 455

<210> SEQ ID NO 11
<211> LENGTH: 1386
<212> TYPE: DNA
<213> ORGANISM: Homo sapiens

<400> SEQUENCE: 11

```
atggcgcccg tcgccgtctg ggccgcgctg gccgtcggac tggagctctg ggctgcggcg      60
cacgccttgc ccgcccaggt ggcatttaca ccctacgccc ggagcccgg gagcacatgc     120
cggctcagag aatactatga ccagacagct cagatgtgct gcagcaaatg ctcgccgggc     180
caacatgcaa aagtcttctg taccaagacc tcggacaccg tgtgtgactc ctgtgaggac     240
agcacataca cccagctctg gaactgggtt cccgagtgct tgagctgtgg ctcccgctgt     300
agctctgacc aggtggaaac tcaagcctgc actcgggaac agaaccgcat ctgcaccctg     360
aggcccggct ggtactgcgc gctgagcaag caggaggggt gccggctgtg cgcgccgctg     420
cgcaagtgcc gcccgggctt cggcgtggcc agaccaggaa ctgaaacatc agacgtggtg     480
tgcaagccct gtgccccggg gacgttctcc aacacgactt catccacgga tatttgcagg     540
ccccaccaga tctgtaacgt ggtggccatc cctgggaatg caagcatgga tgcagtctgc     600
acgtccacgt cccccacccg gagtatggcc caggggcag tacacttacc ccagccagtg     660
tccacacgat cccaacacac gcagccaact ccagaaccca gcactgctcc aagcacctcc     720
ttcctgctcc caatgggccc cagcccccca gctgaaggga gcactggcga cttcgctctt     780
ccagttggac tgattgtggg tgtgacagcc ttgggtctac taataatagg agtggtgaac     840
tgtgtcatca tgacccaggt gaaaaagaag cccttgtgcc tgcagagaga agccaaggtg     900
cctcacttgc ctgccgataa ggcccggggt acacagggcc ccgagcagca gcacctgctg     960
atcacagcgc cgagctccag cagcagctcc ctggagagct cggccagtgc gttggacaga    1020
agggcgccca ctcggaacca gccacaggca ccaggcgtgg aggccagtgg gccggggag    1080
gcccgggcca gcaccgggag ctcagattct tcccctggtg ccatgggac ccaggtcaat    1140
gtcacctgca tcgtgaacgt ctgtagcagc tctgaccaca gctcacagtg ctcctcccaa    1200
gccagctcca atgggagaca cagattcc agccctcgg agtccccgaa ggacgagcag    1260
gtccccttct ccaaggagga atgtgccttt cggtcacagc tggagacgcc agagaccctg    1320
ctggggagca ccgaagagaa gccctgccc cttggagtgc ctgatgctgg gatgaagccc    1380
agttaa                                                             1386
```

<210> SEQ ID NO 12
<211> LENGTH: 461
<212> TYPE: PRT
<213> ORGANISM: Homo sapiens

<400> SEQUENCE: 12

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

```
Ala Pro Glu Pro Gly Ser Thr Cys Arg Leu Arg Glu Tyr Asp Gln
         35                  40                  45

Thr Ala Gln Met Cys Cys Ser Lys Cys Ser Pro Gly Gln His Ala Lys
 50                  55                  60

Val Phe Cys Thr Lys Thr Ser Asp Thr Val Cys Asp Ser Cys Glu Asp
 65                  70                  75                  80

Ser Thr Tyr Thr Gln Leu Trp Asn Trp Val Pro Glu Cys Leu Ser Cys
                 85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
            115                 120                 125

Ser Lys Gln Glu Gly Cys Arg Leu Cys Ala Pro Leu Arg Lys Cys Arg
130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
            195                 200                 205

Met Ala Pro Gly Ala Val His Leu Pro Gln Pro Val Ser Thr Arg Ser
210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
                260                 265                 270

Leu Leu Ile Ile Gly Val Val Asn Cys Val Ile Met Thr Gln Val Lys
            275                 280                 285

Lys Lys Pro Leu Cys Leu Gln Arg Glu Ala Lys Val Pro His Leu Pro
290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
            355                 360                 365

Asp Ser Ser Pro Gly Gly His Gly Thr Gln Val Asn Val Thr Cys Ile
            370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
            435                 440                 445

Leu Pro Leu Gly Val Pro Asp Ala Gly Met Lys Pro Ser
```

<210> SEQ ID NO 13
<211> LENGTH: 1710
<212> TYPE: DNA
<213> ORGANISM: Homo sapiens

<400> SEQUENCE: 13

```
atgaaagtgt tactcagact tatttgtttc atagctctac tgatttcttc tctggaggct      60
gataaatgca aggaacgtga agaaaaaata attttagtgt catctgcaaa tgaaattgat     120
gttcgtccct gtcctcttaa cccaaatgaa cacaaaggca ctataacttg gtataaagat     180
gacagcaaga cacctgtatc tacagaacaa gcctccagga ttcatcaaca caaagagaaa     240
ctttggtttg ttcctgctaa ggtggaggat tcaggacatt actattgcgt ggtaagaaat     300
tcatcttact gcctcagaat taaaataagt gcaaaatttg tggagaatga gcctaactta     360
tgttataatg cacaagccat atttaagcag aaactacccg ttgcaggaga cggaggactt     420
gtgtgccctt atatggagtt ttttaaaaat gaaaataatg agttacctaa attacagtgg     480
tataaggatt gcaaacctct acttcttgac aatatacact ttagtggagt caaagatagg     540
ctcatcgtga tgaatgtggc tgaaaagcat agagggaact atacttgtca tgcatcctac     600
acatacttgg gcaagcaata tcctattacc cgggtaatag aatttattac tctagaggaa     660
aacaaaccca aaggcctgt gattgtgagc ccagctaatg acaatggaag agtagacttg     720
ggatcccaga tacaattgat ctgtaatgtc accggccagt tgagtgacat tgcttactgg     780
aagtggaatg ggtcagtaat tgatgaagat gacccagtgc taggggaaga ctattacagt     840
gtggaaaatc ctgcaaacaa agaaggagt accctcatca cagtgcttaa tatatcggaa     900
attgaaagta gatttatata acatccattt acctgttttg ccaagaatac acatggtata     960
gatgcagcat atatccagtt aatatatcca gtcactaatt ccagaagca catgattggt    1020
atatgtgtca cgttgacagt cataattgtg tgttctgttt tcatctataa aatcttcaag    1080
attgacattg tgctttggta cagggattcc tgctatgatt ttctcccaat aaaagcttca    1140
gatggaaaga cctatgacgc atatatactg tatccaaaga ctgttgggga agggtctacc    1200
tctgactgtg atatttttgt gtttaaagtc ttgcctgagg tcttggaaaa acagtgtgga    1260
tataagctgt tcatttatgg aagggatgac tacgttgggg aagacattgt tgaggtcatt    1320
aatgaaaacg taagaaaag cagaagactg attatcattt tagtcagaga acatcaggc    1380
ttcagctggc tggtggttc atctgaagag caaatagcca tgtataatgc tcttgttcag    1440
gatggaatta aagttgtcct gcttgagctg gagaaaatcc aagactatga gaaatgccca    1500
gaatcgatta aattcattaa gcagaaacat gggctatcc gctggtcagg gactttaca    1560
cagggaccac agtctgcaaa gacaaggttc tggaagaatg tcaggtacca catgccagtc    1620
cagcgacggt caccttcatc taaacaccag ttactgtcac cagccactaa ggagaaactg    1680
caaagagagg ctcacgtgcc ctctcgggtag                                    1710
```

<210> SEQ ID NO 14
<211> LENGTH: 569
<212> TYPE: PRT
<213> ORGANISM: Homo sapiens

<400> SEQUENCE: 14

```
Met Lys Val Leu Leu Arg Leu Ile Cys Phe Ile Ala Leu Leu Ile Ser
1               5                   10                  15
```

-continued

```
Ser Leu Glu Ala Asp Lys Cys Lys Glu Arg Glu Lys Ile Ile Leu
             20                  25                  30

Val Ser Ser Ala Asn Glu Ile Asp Val Arg Pro Cys Pro Leu Asn Pro
             35                  40                  45

Asn Glu His Lys Gly Thr Ile Thr Trp Tyr Lys Asp Asp Ser Lys Thr
         50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                 85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
            115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
            195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
            275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
            355                 360                 365

Asp Ser Cys Tyr Asp Phe Leu Pro Ile Lys Ala Ser Asp Gly Lys Thr
    370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
```

| | | 435 | | | | 440 | | | | 445 | | |
|---|---|---|---|---|---|---|---|---|---|---|---|---|
Arg Leu Ile Ile Ile Leu Val Arg Glu Thr Ser Gly Phe Ser Trp Leu
450 455 460

Gly Gly Ser Ser Glu Glu Gln Ile Ala Met Tyr Asn Ala Leu Val Gln
465 470 475 480

Asp Gly Ile Lys Val Leu Leu Glu Leu Glu Lys Ile Gln Asp Tyr
485 490 495

Glu Lys Met Pro Glu Ser Ile Lys Phe Ile Lys Gln Lys His Gly Ala
500 505 510

Ile Arg Trp Ser Gly Asp Phe Thr Gln Gly Pro Gln Ser Ala Lys Thr
515 520 525

Arg Phe Trp Lys Asn Val Arg Tyr His Met Pro Val Gln Arg Arg Ser
530 535 540

Pro Ser Ser Lys His Gln Leu Leu Ser Pro Ala Thr Lys Glu Lys Leu
545 550 555 560

Gln Arg Glu Ala His Val Pro Leu Gly
565

<210> SEQ ID NO 15
<211> LENGTH: 1197
<212> TYPE: DNA
<213> ORGANISM: Homo sapiens

<400> SEQUENCE: 15

```
atgttgcgct tgtacgtgtt ggtaatggga gtttctgcct tcacccttca gcctgcggca    60
cacacagggg ctgccagaag ctgccggttt cgtggggaggc attacaagcg ggagttcagg   120
ctggaagggg agcctgtagc cctgaggtgc ccccaggtgc cctactggtt gtgggcctct   180
gtcagccccc gcatcaacct gacatggcat aaaaatgact ctgctaggac ggtcccagga   240
gaagaagaga cacggatgtg ggcccaggac ggtgctctgt ggcttctgcc agccttgcag   300
gaggactctg gcacctacgt ctgcactact agaaatgctt cttactgtga caaaatgtcc   360
attgagctca gagttttga gaatacagat gctttcctgc cgttcatctc atacccgcaa   420
atttaacct tgtcaacctc tggggtatta gtatgccctg acctgagtga attcacccgt   480
gacaaaactg acgtgaagat tcaatggtac aaggattctc ttcttttgga taaagacaat   540
gagaaatttc taagtgtgag ggggaccact cacttactcg tacacgatgt ggccctggaa   600
gatgctggct attccgctg tgtcctgaca tttgcccatg aaggccagca atacaacatc   660
actaggagta ttgagctacg catcaagaaa aaaaagaag agaccattcc tgtgatcatt   720
tcccccctca agaccatatc agcttctctg gggtcaagac tgacaatccc gtgtaaggtg   780
tttctgggaa ccggcacacc cttaaccacc atgctgtggt ggacggccaa tgacacccac   840
atagagagcg cctacccggg aggccgcgtg accgaggggc acgccagga atattcagaa   900
aataatgaga actacattga agtgccattg atttttgatc ctgtcacaag agaggatttg   960
cacatggatt ttaaatgtgt tgtccataat accctgagtt tcagacact acgcaccaca  1020
gtcaaggaag cctcctccac gttctcctgg ggcattgtgc tggccccact ttcactggcc  1080
ttcttggttt tgggggaat atggatgcac agacggtgca acacagaac tggaaaagca  1140
gatggtctga ctgtgctatg gcctcatcat caagactttc aatcctatcc caagtga    1197
```

<210> SEQ ID NO 16
<211> LENGTH: 398
<212> TYPE: PRT
<213> ORGANISM: Homo sapiens

<400> SEQUENCE: 16

```
Met Leu Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Trp Gly Ile
            340                 345                 350

Val Leu Ala Pro Leu Ser Leu Ala Phe Leu Val Leu Gly Gly Ile Trp
        355                 360                 365

Met His Arg Arg Cys Lys His Arg Thr Gly Lys Ala Asp Gly Leu Thr
    370                 375                 380

Val Leu Trp Pro His His Gln Asp Phe Gln Ser Tyr Pro Lys
385                 390                 395
```

-continued

```
<210> SEQ ID NO 17
<211> LENGTH: 891
<212> TYPE: DNA
<213> ORGANISM: Homo sapiens

<400> SEQUENCE: 17
atgttgcgct tgtacgtgtt ggtaatggga gtttctgcct tcacccttca gcctgcggca      60
cacacagggg ctgccagaag ctgccggttt cgtgggaggc attacaagcg ggagttcagg     120
ctggaagggg agcctgtagc cctgaggtgc ccccaggtgc cctactggtt gtgggcctct     180
gtcagccccc gcatcaacct gacatggcat aaaaatgact ctgctaggac ggtcccagga     240
gaagaagaga cacggatgtg ggcccaggac ggtgctctgt ggcttctgcc agccttgcag     300
gaggactctg gcacctacgt ctgcactact agaaatgctt cttactgtga caaaatgtcc     360
attgagctca gagttttga gaatacagat gctttcctgc cgttcatctc ataccccgcaa     420 attttaacct tgtcaacctc tggggtatta gtatgccctg acctgagtga attcacccgt     480
gacaaaactg acgtgaagat tcaatggtac aaggattctc ttcttttgga taaagacaat     540
gagaaatttc taagtgtgag ggggaccact cacttactcg tacacgatgt ggccctggaa     600
gatgctggct attaccgctg tgtcctgaca tttgcccatg aaggccagca atacaacatc     660
actaggagta ttgagctacg catcaagaaa aaaaagaag agaccattcc tgtgatcatt     720 tccccctca agaccatatc agcttctctg gggtcaagac tgacaatccc gtgtaaggtg     780
tttctgggaa ccggcacacc cttaaccacc atgctgtggt ggacggccaa tgacacccac     840
atagagagcg cctacccggg aggccgcgtg accgaggggc cacgccagta a              891

<210> SEQ ID NO 18
<211> LENGTH: 296
<212> TYPE: PRT
<213> ORGANISM: Homo sapiens

<400> SEQUENCE: 18

Met Leu Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
```

-continued

```
            180                 185                 190
Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
        210                 215                 220

Glu Leu Arg Ile Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
                260                 265                 270

Trp Trp Thr Ala Asn Asp Thr His Ile Glu Ser Ala Tyr Pro Gly Gly
        275                 280                 285

Arg Val Thr Glu Gly Pro Arg Gln
        290                 295
```